United States Patent
Shahinian et al.

(10) Patent No.: US 9,931,023 B2
(45) Date of Patent: Apr. 3, 2018

(54) STEREO IMAGING MINIATURE ENDOSCOPE WITH SINGLE IMAGING CHIP AND CONJUGATED MULTI-BANDPASS FILTERS

(76) Inventors: Hrayr Karnig Shahinian, Beverly Hills, CA (US); Youngsam Bae, Los Angeles, CA (US); Harish M. Manohara, Arcadia, CA (US); Victor E. White, Altadena, CA (US); Kirill V. Shcheglov, Los Angeles, CA (US); Robert S. Kowalczyk, Valencia, CA (US)

( * ) Notice: Subject to any disclaimer, the term of this patent is extended or adjusted under 35 U.S.C. 154(b) by 134 days.

(21) Appl. No.: 12/946,839

(22) Filed: Nov. 15, 2010

(65) Prior Publication Data

US 2011/0115882 A1     May 19, 2011

Related U.S. Application Data

(60) Provisional application No. 61/261,217, filed on Nov. 13, 2009.

(51) Int. Cl.
*A61B 1/06*     (2006.01)
*A61B 1/00*     (2006.01)
(Continued)

(52) U.S. Cl.
CPC .......... *A61B 1/00193* (2013.01); *A61B 1/045* (2013.01); *A61B 1/05* (2013.01);
(Continued)

(58) Field of Classification Search
USPC .......................................................... 348/45
See application file for complete search history.

(56) References Cited

U.S. PATENT DOCUMENTS 1,960,011 A * 5/1934 Ives ............................. 396/330
2,255,631 A    9/1941 Shulman
(Continued)

FOREIGN PATENT DOCUMENTS

EP    1371321 A1    12/2003
EP    1880657 A1    1/2008
(Continued)

OTHER PUBLICATIONS

Y.S. Heo, "Illumination and Camera Invariant Stereo Matching," Computer Vision and Pattern Recognition, 2008. CVPR 2008. IEEE Conference, vol., No., pp. 1-8, Jun. 23-28, 2008.
(Continued)

*Primary Examiner* — Mikhail Itskovich

(57) ABSTRACT

A dual objective endoscope for insertion into a cavity of a body for providing a stereoscopic image of a region of interest inside of the body including an imaging device at the distal end for obtaining optical images of the region of interest (ROI), and processing the optical images for forming video signals for wired and/or wireless transmission and display of 3D images on a rendering device. The imaging device includes a focal plane detector array (FPA) for obtaining the optical images of the ROI, and processing circuits behind the FPA. The processing circuits convert the optical images into the video signals. The imaging device includes right and left pupil for receiving a right and left images through a right and left conjugated multi-band pass filters. Illuminators illuminate the ROI through a multi-band pass filter having three right and three left pass bands that are matched to the right and left conjugated multi-band pass filters. A full color image is collected after three or six sequential illuminations with the red, green and blue lights.

37 Claims, 19 Drawing Sheets

(51) Int. Cl.
*H04N 13/02* (2006.01)
*A61B 1/045* (2006.01)
*A61B 1/05* (2006.01)

(52) U.S. Cl.
CPC .......... *A61B 1/0638* (2013.01); *A61B 1/0646* (2013.01); *H04N 13/021* (2013.01); *H04N 13/0214* (2013.01); *H04N 13/0253* (2013.01); *H04N 13/0257* (2013.01); *A61B 1/00183* (2013.01); *A61B 1/00188* (2013.01); *A61B 1/0607* (2013.01); *A61B 1/0684* (2013.01)

(56) References Cited

U.S. PATENT DOCUMENTS

| | | |
|---|---|---|
| 3,870,037 A | 3/1975 | Cadariu et al. |
| 4,761,066 A | 8/1988 | Carter |
| 4,873,572 A | 10/1989 | Miyazaki et al. |
| 4,877,307 A | 10/1989 | Kalmanash |
| 5,105,269 A | 4/1992 | Nakamura et al. |
| 5,192,969 A | 3/1993 | Igarashi et al. |
| 5,222,477 A | 6/1993 | Lia |
| 5,305,098 A | 4/1994 | Matsunaka et al. |
| 5,436,655 A | 7/1995 | Hiyama |
| 5,459,605 A | 10/1995 | Kempf |
| 5,471,237 A | 11/1995 | Shipp |
| 5,494,483 A | 2/1996 | Adair |
| 5,603,687 A | 2/1997 | Hori et al. |
| 5,743,847 A | 4/1998 | Nakamura et al. |
| 5,751,341 A | 5/1998 | Chaleki et al. |
| 5,810,716 A | 9/1998 | Mukherjee et al. |
| 5,828,487 A | 10/1998 | Greening et al. |
| 5,835,194 A | 11/1998 | Morton |
| 5,964,696 A | 10/1999 | Mihalca et al. |
| 5,984,939 A | 11/1999 | Yoon |
| 6,050,939 A | 4/2000 | Pak Wai |
| 6,306,082 B1 | 10/2001 | Takahashi et al. |
| 6,419,626 B1 | 7/2002 | Yoon |
| 6,517,479 B1 | 2/2003 | Sekiya et al. |
| 6,593,957 B1 | 7/2003 | Christie |
| 6,624,935 B2 | 9/2003 | Weissman et al. |
| 6,916,286 B2 | 7/2005 | Kazakevich |
| RE39,342 E | 10/2006 | Starks et al. |
| 7,153,259 B2 | 12/2006 | Matsuzawa et al. |
| 7,154,527 B1 | 12/2006 | Goldstein et al. |
| 7,241,262 B2 | 7/2007 | Adler et al. |
| 7,553,277 B2 | 6/2009 | Hoefig et al. |
| 7,601,119 B2 | 10/2009 | Shahinian |
| 7,621,869 B2 | 11/2009 | Ratnakar |
| 2002/0049367 A1 | 4/2002 | Irion et al. |
| 2002/0154215 A1* | 10/2002 | Schechterman et al. ....... 348/51 |
| 2003/0125608 A1 | 7/2003 | Igarashi |
| 2003/0174208 A1 | 9/2003 | Glukhovsky et al. |
| 2003/0233024 A1 | 12/2003 | Ando |
| 2004/0019255 A1 | 1/2004 | Sakiyama |
| 2004/0070667 A1 | 4/2004 | Ando |
| 2005/0228230 A1 | 10/2005 | Schara et al. |
| 2005/0261548 A1 | 11/2005 | Machiya et al. |
| 2006/0224040 A1* | 10/2006 | Khait et al. .................... 600/102 |
| 2006/0247495 A1 | 11/2006 | Bacher et al. |
| 2008/0281154 A1 | 11/2008 | Gono et al. |
| 2008/0284982 A1* | 11/2008 | Richards et al. ............... 352/38 |
| 2009/0187072 A1 | 7/2009 | Manohara et al. |

FOREIGN PATENT DOCUMENTS

| | | |
|---|---|---|
| JP | 06-237892 | 8/1994 |
| WO | WO 2000/050927 | 8/2000 |
| WO | 2002037142 A2 | 5/2002 |
| WO | 2003098913 A2 | 11/2003 |

OTHER PUBLICATIONS

J.L. Garb, "Using GIS for spatial analysis of rectal lesions in the human body," International Journal of Health Geographics, 2007, 6:11, Published online Mar. 15, 2007. doi: 10.1186/1476-072X-6-11. PMCID: PMC1839078 BioMed Central Ltd.
J.P. Rice, "A hyperspectral image projector for hyperspectral imagers," SPIE vol. 6565, 65650C, (2007).
J.P. Rice, "Hyperspectral image projectors for radiometric applications," BIPM and IOP Publishing Ltd, Metrologia 43 ( 2006) S61-S65.
J.P. Rice, "Development of hyperspectral image projectors," SPIE vol. 6297, 629701, (2006).
J.M. Medina, "Binocular interactions in random chromatic changes at isoluminance," Opt. Soc. Am., 2006, vol. 23, No. 2, pp. 239-246.
A. Szold, "Seeing is believing-Visualization systems in endoscopic surgery (video, HDTV, stereoscopy, and beyond)," Surgical Endoscopy, 19:55, pp. 730-733, Springer, 2005.
U. D. A Mueller-Richter,"Possibilities and limitations of current stereo-endoscopy," Journal of Surgical Endoscopy, Springer, New York, ISSN 0930-2794 (Print) 1432-2218 (Online) Issue vol. 18, No. 6, Jun. 2004, 18: pp. 942-947.
M.A. Weissman, "Stereo parallax and Disnparity in Single-Lens Stereoscopy," Stereoscopic Displays and Virtual Reality Systems VII, SPIE 3987, pp. 312-320, Apr. 2000.
G.A. Lester, "Ferroelectric liquid crystal device for a single camera stereoscopic endoscope system," Electronics Letters, 1997, vol. 33, No. 10, pp. 857-858.
G.L. Zimmerman, "Perception at Equiluminance: An Adaptive Model of Motion Metamers," Circuits and Systems, 1994., Proceedings of the 37th Midwest Symposium on , vol. 1, No., pp. 577-580 vol. 1, Aug. 3-5, 1994.
Y. Takemura, "Stereoscopic Video Movie Camera Using 300k Pixel IT-CCD Sensors," IEEE Transactions on Consumer Electronics, Feb. 1991, vol. 37, No. 1, pp. 39-44.
E. Badique, "Use of color image correlation in the retrieval of gastric surface topography by endoscopic stereopair matching," Applied Optics, 1988, vol. 27, No. 5, pp. 941-948.
N. Ohyama, "Compensation of motion blur in CCD color endoscope images," Opt. Soc. Am., 2006, Applied Optics, 1987, vol. 26, No. 5, pp. 909-912.
P. Breedveld and M. Wentink, "Eye-hand coordination in laparoscopy—An overview of experiments and supporting aids," Min Invas Ther & Allied Technol 2001: 155-162, 10(3).
Keijirou Itakura, et al., "A 1-mm 50 k-Pixel IT CCD Image Sensor for Miniature Camera System," IEEE Transactions on Electron Devices, Jan. 2000, 65-70, vol. 47, No. 1.
Jacques Duparré, et al., "Thin compound-eye camera," Applied Optics, May 20, 2005, pp. 2949-2956, vol. 44, No. 15.
Jun Tanida, et al., "Color imaging with an integrated compound imaging system," Optics Express, Sep. 8, 2003, 2019-2117, vol. 11, No. 18.
Jun Tanida, et al., "Thin observation module by bound optics (TOMBO): concept and experimental verification," Applied Optics, Apr. 10, 2001, 1806-1813, vol. 40, No. 11.
Ikeda, M., Sagawa, K., "Binocular color fusion limit," J. of the Optical Society of America, 69(2), 316-321, (Feb. 1979).
Dudley, D., Duncan, W. M., Slaughter, J., "Emerging digital miromirror device (DMD) applications," Proceedings of SPIE 4985, 14-25 (2003).
Hovis, J. K., "Review of Dichoptic Color Mixing," Optometry and Vision Science, 66(3), 181-190 (1998).
Lambooij, M., Ijsselsteijn, W., "Visual discomfort and visual fatigue of stereoscopic display: A review," J. of Imaging science and technology, 53(3), 030201 (2009).
DooHyun Lee and InSo Kweon, "A Novel Stereo Camera System by a Biprism," IEEE Transactions on Robotics and Automation, 16(5), 528-541, (Oct. 2000).
Mikko Kyto, Mikko Nuutinen, Pirkko Oittinen, "Method for measuring stereo camera depth accuracy based on stereoscopic vision," OAalto University School of Science and Technology, Department of Media Technology, Otaniementie 17, Espoo, Finland.

(56) References Cited

OTHER PUBLICATIONS

Qin, D., Takamatsu, M., Nakashima, Y., Qin, X., "Change of wavelength difference limit for binocular color fusion with wavelength and brightness of stimuli," J. of Light and Visual Environment, 30(1), 43-45 (2006).
Jung, Y. J., Sohn, H., Lee, S., Ro, Y. M., and Park, H. W., "Quantitative measurement of binocular color fusion limit for non-spectral colors.," Optics express, 19(8), 7325-7338 (2011).
Planar Systems Inc., "SD1710 Pruduct User's Guide," 1-12 (2005).
CRI Varispec, " Liquid Crystal Tuneable Filters," 1-12 (2005).
Avi Yaron, Mark Shechterman and Nadav Horesh, "Blur spot limitations in distal endoscope sensors," Proc. SPIE 6055, Stereoscopic Displays and Virtual Reality Systems XIII, 605509 (Jan. 27, 2006).

\* cited by examiner

STEREO IMAGING MINIATURE ENDOSCOPE WITH SINGLE IMAGING CHIP AND CONJUGATED MULTI-BANDPASS FILTERS

This application claims the benefits of U.S. Provisional Patent Application Ser. No. 61/261,217 filed Nov. 13, 2009, which is incorporated herein by reference in its entirety.

The invention described herein was made in the performance of work under a NASA contract, and is subject to the provisions of Public Law 96-517 (35 USC 202) in which the Contractor has elected to retain title.

The present system relates to at least one of a system, method, user interface (UI), and apparatus for providing stereoscopic images and, more particularly, to small-diameter stereoscopic endoscopes for minimally invasive surgery (MIS) as well as to micro-robotic stereoscopic imagers for providing images for space exploration.

Stereoscopic vision imaging is a well known technology and has been used effectively to provide depth perception to displayed images. Stereoscopic imaging devices often use a three-dimensional camera to capture images and render three-dimensional (3D) images which may be viewed with realistic depth using a 3D-image-rendering device such as a 3D display. Such realism is of great importance when performing MIS surgery as minimizes surgical errors and achieves high efficiency during a MIS procedure. With the advancement of MIS techniques, physical injury due to incisions at a surgical site is minimized using incisions are typically about 4 mm in across. However, conventional stereoscopic imaging devices are often bulky as they require two cameras placed side by side which increases the size of the imaging device. Unfortunately, as MIS typically requires the use of endoscopes which are between 2 and 4 mm, conventional imaging devices (e.g., cameras, etc.) cannot be used because of size limitations.

The present system discloses a system, method, apparatus, and computer program portion (hereinafter each of which may be referred to as system unless the context indicates otherwise) suitable to provide stereoscopic images in an MIS and/or space environment. Accordingly, the present system discloses a small-diameter high-definition stereoscopic endoscope or boroscope (hereinafter commonly called an endoscope) which may have diameter which is less than 4 mm, such as 1-4 mm including any sizes therebetween, such as 3-4 mm, 2-4 mm, 2-3 mm, etc. However, other ranges are also envisioned. There is also disclosed a micro-robotic stereoscopic imaging system suitable for spacecraft which can provide stereoscopic images using a stereoscopic imaging apparatus which may be robotically manipulated and suitable for space exploration. In accordance with an embodiment of the present system, there is disclosed a stereoscopic imaging device which uses a single Focal Plane Array (FPA) to capture image information related to right and left fields of view and can provide high definition (e.g., 1000×1000 pixel resolution) images.

The present systems include stereoscopic endoscopes with Conjugated Multi-Bandpass Filters (CMBFs) covering right and left pupils which may be formed by a single lens having right and left pupil portions, or two dedicated lenses, one lens for the right pupil and one lens for the left pupil. Further, the endoscopes may have a single bore or dual bores, wherein in the case of a dual bore endoscope, two lenses are provided, one lens in each bore for use as a right and left pupils. The single bore endoscope may have one or two lenses. Having a single bore endoscope with a single lens, with conjugated multi-bandpass filters covering right and left pupils of the single objective lens, is less complex and less costly, and provides for a smaller endoscope as compared to the dual bore endoscope, and thus allows for further miniaturization. Further, using conjugated multi-bandpass filters covering right and left pupils allows for desired color(s) to pass through the filters while blocking other colors. This is achieved without active shutters, such as without switchable liquid crystal (LC) shutter or mechanical shutters that open or close or move in one direction or another to close one pupil while the other pupil is open. Of course, if desired, LC switches may be used in front of the pupils and controlled (such as by a processor) to selectively switch on only one pupil at time. Similarly, if desired, a mechanical shutter may be used and moved back and forth to open one pupil while blocking the other pupil.

Conjugated multi-bandpass filters automatically block undesired light color from entering a pupil provide several advantages, such as not requiring energy needed in LC shutters, and not require moving parts used in mechanical shutters. Accordingly, energy consumption and failure are reduced and reliability increased while producing high definition images in a small area by multispectral imaging.

The CMBF creates two viewpoints in a single lens. The filters are called "conjugated" because the spectral passbands of one filter do not overlap with those of the other filters; instead the spectral passbands are interdigitated (see FIG. 9), where each color band is divided into right and left colors, such right red $R_R$, left red $R_L$, right green $G_R$, left green $G_L$, right blue $B_R$ and left blue $B_L$. In one embodiment, circular CMBFs are used which are each cut in half and joined with the conjugated other half to form the CMBF full circle covering a portion or the entire single objective lens and providing right and left pupil portions, so that the full circle CMBF can fit along with other circular optical elements, such as over a circular single objective lens. When a light band matching to a bandpass of one CMBF is illuminated, the one half CMBF passes a light band, but the other half CMBF stops the same light band. A region of interest is illuminated using a series of light bands matching to the passbands of the CMBFs for capturing multispectral images and forming stereoscopic 3D images.

It should be noted that each sub-color, such as right and left reds $R_R$, $R_L$ does not exactly match the full red color due to the half missing band, where each sub color is knows as a metamer. However, binocular color mixture appears to be taking place where the final stereo 3D images have high definition and satisfactory color richness to allow depth perception and color distinction for various applications, such as endoscope-based surgeries, wireless endoscopy, navigations for miniature robots such as rovers or airborne robots, deployable robotic arms where monitoring depth information is crucial, as well as other areas where depth perception and/or color distinction are important.

According to another aspect of the present system, there is disclosed an endoscope for providing a stereoscopic three dimensional (3-D) image of a region of interest inside of a body, the endoscope including one or more of: a housing having a distal end and a proximal end, the distal end being insertable into a cavity of the body, an imaging device at the distal end for obtaining optical images of the region of interest, and processing the optical images for forming video signals; and a cable between the imaging device and the proximal end for connecting the imaging device to an illumination source and/or a display, the cable including a signal line for providing the video signals to the display for displaying the optical images of the region of interest; wherein the imaging device may include: a single focal plane detector array at a front end facing the region of interest for obtaining the optical images, and processing circuits at a back end behind the single focal plane detector array so that the processing circuits does not enlarge a cross section of the imaging device, the processing circuits being configured to convert the optical images into the video signals; a right pupil for receiving a right image through a right multi-band pass filter having right three pass bands ($R_R G_R B_R$): a left pupil for receiving a left image through a left multi-band pass filter having left three pass bands ($R_L G_L B_L$), wherein the right multi-band pass filter having the right three pass bands ($R_R G_R B_R$) is the complement of the left multi-band pass filter having left three pass bands ($R_L G_L B_L$); a lens system for imaging the right image and the left image directly on the single focal plane detector array; and/or illuminators for illuminating the region of interest through a multi-band pass filter having the right three pass bands ($R_R G_R B_R$) and the left three pass bands ($R_L G_L B_L$), wherein the multi-band pass filter is matched to the right multi-band pass filter (of the right pupil) and the left multi-band pass filter (of the left pupil) so that when the right pupil receives light reflected from the region of interest then the left pupil is blocked from receiving the light.

According to the present system, the right three pass bands ($R_R G_R B_R$) may be separated by right stop bands and the left three pass bands ($R_L G_L B_L$) may be separated by left stop bands, the right stop bands matching the left three pass ($R_L G_L B_L$) and the left stop bands matching the right three pass bands ($R_R G_R B_R$). Further, the illuminators may, under the control of the controller, provide illumination to illuminate the imaging device (625) through the multi-band pass filter so that the region of interest is illuminated one at a time by light within one of the right three pass bands ($R_R G_R B_R$) and the left three pass bands ($R_L G_L B_L$). Further, right three pass bands ($R_R G_R B_R$) and the left three pass bands ($R_L G_L B_L$) may be within a visible spectrum having three primary colors (RGB) so that each primary color (R,G,B) is divided into a right primary color and a left primary color ($R_R R_L$, $G_R G_L$, $B_R B_L$), the right primary color being a metamer of the left primary color.

Further, according to the system, the cable may include: right light guides for providing a right illumination at the illuminators including providing one at a time right sub-lights at the right three pass bands ($R_R G_R B_R$) from the right multi-band pass filter; and/or a left light guide for providing a left illumination at the illuminators including providing one at a time left sub-lights at the left three pass bands ($R_L G_L B_L$) from the left multi-band pass filter.

Moreover, the right multi-band pass filter may be illuminated by a right white light source through a right rotating wheel having an aperture for providing a right white light one at a time to the right multi-band pass filter; and wherein and the left multi-band pass filter may be illuminated by a left white light source through a left rotating wheel having an aperture for providing a left white light one at a time to the left multi-band pass filter; wherein the right and left multi-band pass filters may be located at entrance sides or exit sides of the right light guides and the a left light guide, respectively.

Moreover, it is envisioned that the right multi-band pass filter may be illuminated by a white light source through a single rotating wheel having three apertures for sequentially providing: a red light through a red multi-band pass filter having right-red ($R_R$) and left-red ($R_L$) bands to the right pupil and the left pupil, respectively, a green light through a green multi-band pass filter having right-green ($G_R$) and left-green ($G_L$) bands to the right pupil and the left pupil, respectively, and/or a blue light through a blue multi-band pass filter having right-blue ($B_R$) and left-blue ($B_L$) bands to the right pupil and the left pupil, respectively, wherein a full color image may be collected after three sequential illuminations through the three apertures of the a single rotating wheel. Further, the cable may include light guides illuminated by three right white light sources which may provide a right illumination including providing one at a time right sub-lights at the right three pass bands ($R_R G_R B_R$) from the right multi-band pass filter; the light guides being further illuminated by three left white light sources which may provide a left illumination including providing one at a time left sub-lights at the left three pass bands ($R_L G_L B_L$) from the left multi-band pass filter.

Further, three right white light sources may each have a bandpass filter having one of the right three pass bands ($R_R G_R B_R$), and the three left white light sources may each have a bandpass filter having one of the left three pass bands ($R_L G_L R_L$). The lens system may include a lens configured to image the right image and the left image, one at a time, on substantially an entire area of the single focal plane detector array. Further, a cross section of the imaging device may be substantially circular, oval, or square. The endoscope may further include a controller for time-multiplexing the right image and the left image imaged sequentially on the single focal plane detector array.

The lens system may further include two lenses configured to image the right image on a first portion of the single focal plane detector array, and image the left image on a second portion of the single focal plane detector array. Further, a footprint of the imaging device is substantially identical to a footprint of the single focal plane detector array. Moreover, the imaging device may be formed from stacked layers stacked axially along a longitudinal axis of the endoscope, the imaging device having the single focal plane detector array at the front end and the processing circuits formed on one or more layers stacked at the back end of the imaging device over the single focal plane detector array, the one or more layers being connected to the single focal plane detector array through connection bumps. Further, the imaging device may include a folded substrate having the single focal plane detector array at the front end and the processing circuits at the back end of the imaging device.

According to another aspect of the present system, there is provided a dual objective endoscope for insertion into a cavity of a body which may provide a stereoscopic three-dimensional image of a region of interest inside of the body, the endoscope may include one or more of: a first bore having a first lens for receiving first image rays from the region of interest; a second bore having a second lens for receiving second image rays from the region of interest; illuminators for sequentially illuminating the region of interest with red, green and blue lights; and a single focal point array for simultaneously imaging the first image rays and the second image rays on different first and second areas of the array, wherein a full color image may be collected after three sequential illuminations with the with the red, green and blue lights, respectively. Moreover, the illuminators may be coupled through at least one light guide to at least one light source external to the body for providing the red, green and blue lights. Further at least one light source may include a white light source and a rotating color wheel with three openings covered with red, green and blue filters, respectively, for sequentially providing the red, green and blue lights upon rotation of the color wheel.

It is further envisioned that at least one light source may include red, green and blue light emitting diodes (LEDs) and a controller for sequentially turning on the red, green and blue light sources one at a time. Further, the at least one light guide may include three light guides having red, green and blue filters, respectively; the at least one light source may include a white light source and a wheel; and/or the wheel has an opening that, upon alignment with one light guide of the three light guides when the wheel rotates, may allows the white light to pass through the one light guide, for providing sequential illumination of the three light guides due to rotation of the wheel.

According to yet a further aspect of the present system there is provided a medical imaging system comprising: a rigid shaft having proximal and distal ends and an opening situated between the proximal and distal ends, the shaft defining a longitudinal axis extending between the proximal and distal ends; a rod having proximal and distal ends and situated within the opening; first and second handles coupled to the shaft at the proximal end of the shaft, wherein one of the first and second handles may be coupled to the rod; an imaging portion situated at the distal end of the shaft and coupled to the rod such that displacement of one of the first and second handles towards the other of the first and second handles rotates the camera about a second axis. The medical imaging system may further include a two- or three-dimensional camera coupled to the imaging portion. Moreover, the imaging portion may include an illumination source for providing illumination in a direction of the camera. It is further envisioned that the imaging system may include a rack coupled to the distal end of the rod, wherein the imaging portion may further include a pinion situated at the second axis and coupled to the rack.

According to yet a further aspect of the present system, there is disclosed a medical imaging system including: a rigid shaft having proximal and distal ends and an opening situated between the proximal and distal ends, the shaft defining a longitudinal axis extending between the proximal and distal ends; a rod having proximal and distal ends and situated within the opening; first and second handles coupled to the shaft at the proximal end of the shaft, one of the first or second handles coupled to a proximal end of the rod; and/or an imaging portion situated at the distal end of the shaft and coupled to a distal end of the rod such that displacement of one of the first and second handles towards the other of the first and second handles rotates the camera about a second axis.

A two- or three-dimensional camera may be coupled to the imaging portion. Further, imaging portion may further include an illumination source for providing illumination in a direction of the camera. Moreover, a rack may be coupled to the distal end of the rod, and the rack may include a plurality of teeth. Moreover, a pinion may be coupled to the rack and have an axis which is parallel to the second axis. Further, the camera may have a viewing direction which can rotate more than 120 degrees about the second axis. Accordingly, the camera may have a viewing direction which projects substantially forward or rearward along the longitudinal axis of the rigid shaft.

According to yet another aspect of the present system, there is disclosed an endoscope system for obtaining three dimension (3D) images, the endoscope system may include: a multi-bandpass filter which sequentially passes a different color spectrum of light of a plurality of color spectrums of light during an image illumination interval such that a different color of light is passed during each image illumination interval of a plurality of image illumination intervals which form an image illumination period; an image capture portion which sequentially captures a plurality of images each corresponding with a different color spectrum of light which passes through the multi-bandpass filter during a corresponding image illumination interval of the plurality of image illumination intervals; an image processing portion which processes the sequentially captured plurality of images for each image illumination interval of and forms corresponding 3D image information corresponding with a plurality of the sequentially captured plurality of images; and/or a three dimensional display which may render the 3D image information.

Moreover, the endoscope may include an illumination device including at least one source configured to sequentially output the different color spectrum of light during each image illumination interval such that different color spectrums of light are output during any two successive image illumination intervals of the plurality of image illumination intervals. Further, the illumination device includes: a motor; and/or a disk having one or more openings covered with at least one multi-bandpass filter and coupled to the motor, wherein the motor rotates the disk at a rotational frequency which is inversely related to image illumination period for sequentially providing different color spectrum of light during each image illumination period or interval.

Moreover, in accordance with a further aspect of the present system, there is disclosed a medical endoscope system for obtaining three-dimensional images, the medical endoscope system may include: a multi-bandpass optical filter which sequentially passes a different color spectrum of light, of a plurality of color spectrums of light, during a image illumination interval; an image capture portion which sequentially captures a plurality of images each corresponding with a different color spectrum of light which passes through the multi-bandpass optical filter; an image processing portion which processes the sequentially captured plurality of images for each image illumination interval and forms corresponding 3D image information; and/or a three dimensional display which renders the 3D image information. Further, an illumination source may be included and may be configured to sequentially output different color spectrums of light. The multi-bandpass optical filter may further include a disk having one or more openings forming pupils. Moreover, the multi-bandpass filter may be located at a distal end of the endoscope.

According to other aspects of the present system, there is disclosed a method to obtain three dimensional images from an endoscope, the method comprising the acts of: sequentially passing a different color spectrum of light of a plurality of color spectrums of light through a multi-bandpass filter during an image illumination interval such that a different color of light is passed through the multi-bandpass filter during each image illumination interval of a plurality of image illumination intervals which form an image illumination period; sequentially capturing a plurality of images each corresponding with a different color spectrum of light which passes through the multi-bandpass filter during a corresponding image illumination interval of the plurality of image illumination intervals using an image capture portion; processing the sequentially captured plurality of images for each image illumination interval and forming corresponding 3D image information corresponding with the sequentially captured plurality of images using an image processing portion; and/or rendering the 3D image information on a display of the system configured to display three dimensional images. Moreover, the method may include acts of sequentially outputting the different color spectrum of light during each image illumination interval such that different color spectrums of light are output during any two successive image illumination intervals of the plurality of image illumination intervals. Further, the method may include an act of selectively controlling a tunable multi-bandpass optical filter to pass only currently selected spectrum of light of the plurality of color spectrums of light each different from each other. The method may also include an act of synchronizing two or more of an illuminator, a multi-bandpass optical filter, and an image capture portion to operate substantially synchronously with each other to sequentially illuminate the region of interest using different color lights and to sequentially form different color images of the region of interest on a single imaging device or a single Focal Plane Array (FPA).

According to yet other aspects of the present system, there is disclosed a method to obtain three dimensional images from an endoscope, the method may include acts of: sequentially passing a different color spectrum of light, of a plurality of color spectrums of light, during a image illumination interval using a multi-bandpass optical filter; sequentially capturing a plurality of images each corresponding with a different color spectrum of light which passes through the multi-bandpass optical filter using an image capture portion; processing the sequentially captured plurality of images for each image illumination interval and forming corresponding 3D image information using an image processing portion; and/or rendering the 3D image information on a display of the system configured to display three dimensional images. The method may further include an act of situating an optical lens portion of the endoscope between the multi-bandpass optical filter and the image processing portion at a distal end of the endoscope at an end of the endoscope and within a body barrel of the endoscope. Moreover, the method may include an act of forming the main body barrel of the endoscope to have proximal and distal ends and an outside diameter less than 4 mm at the distal end. The method may further include an act of situating the multi-bandpass filter at a distal end of the endoscope.

The invention is explained in further detail, and by way of example, with reference to the accompanying drawings wherein.

Figure 4A:
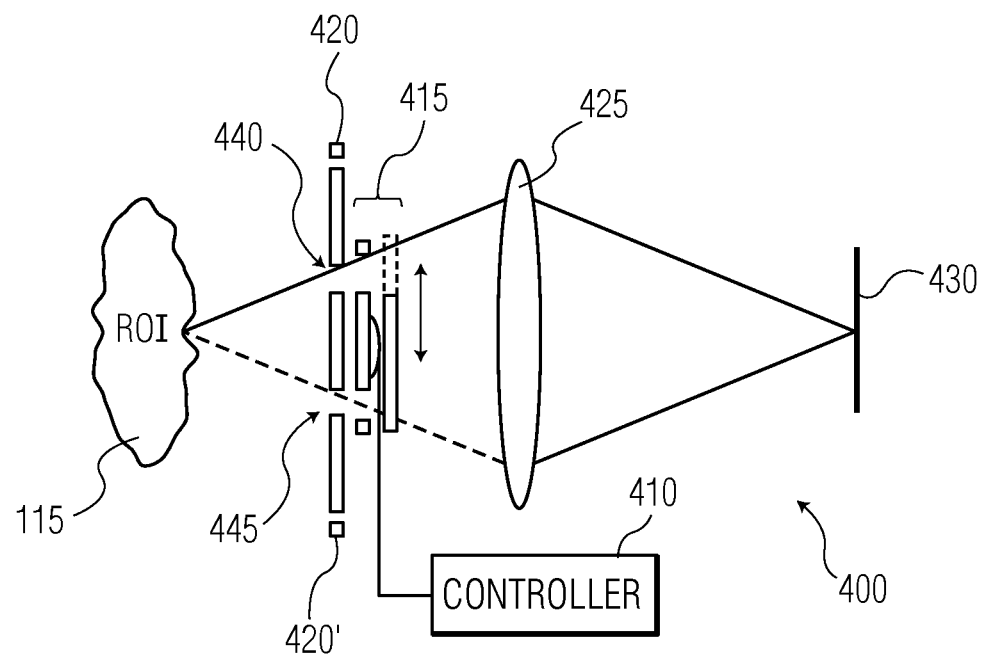
Figure 4B:
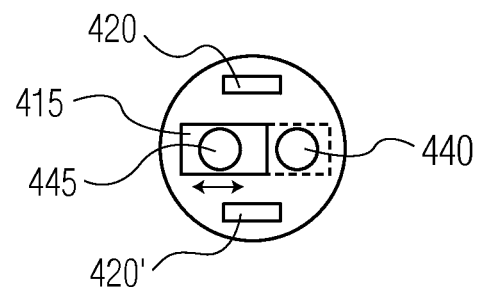
Figure 5:
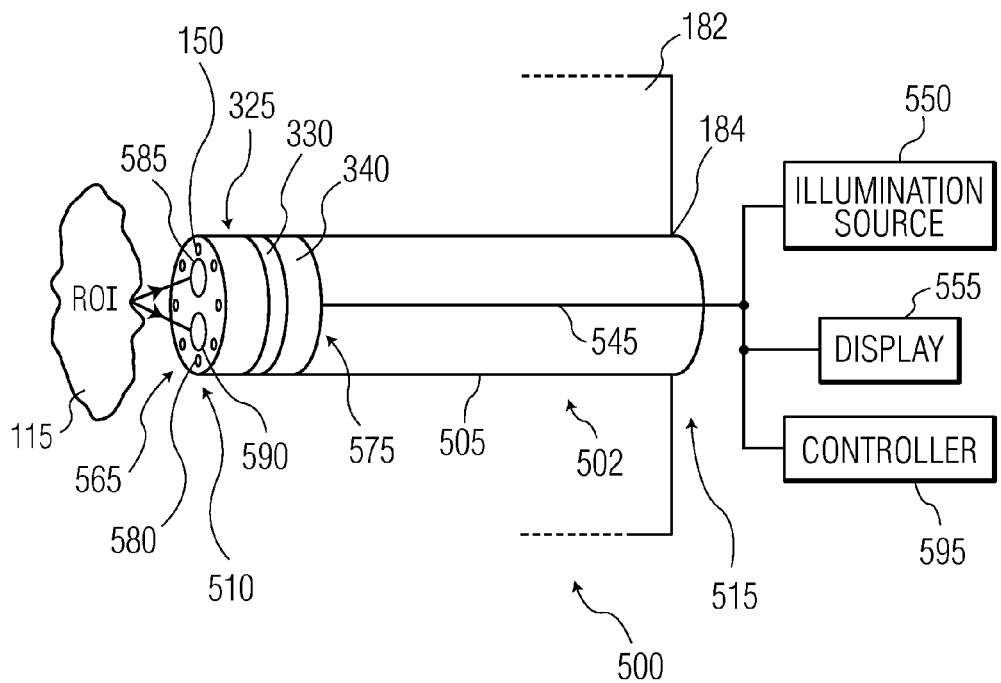
Figure 6:
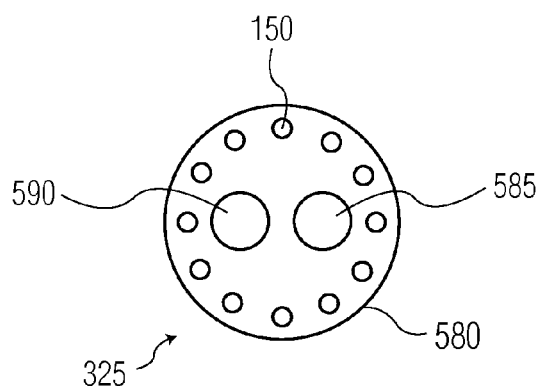
Figure 7A:
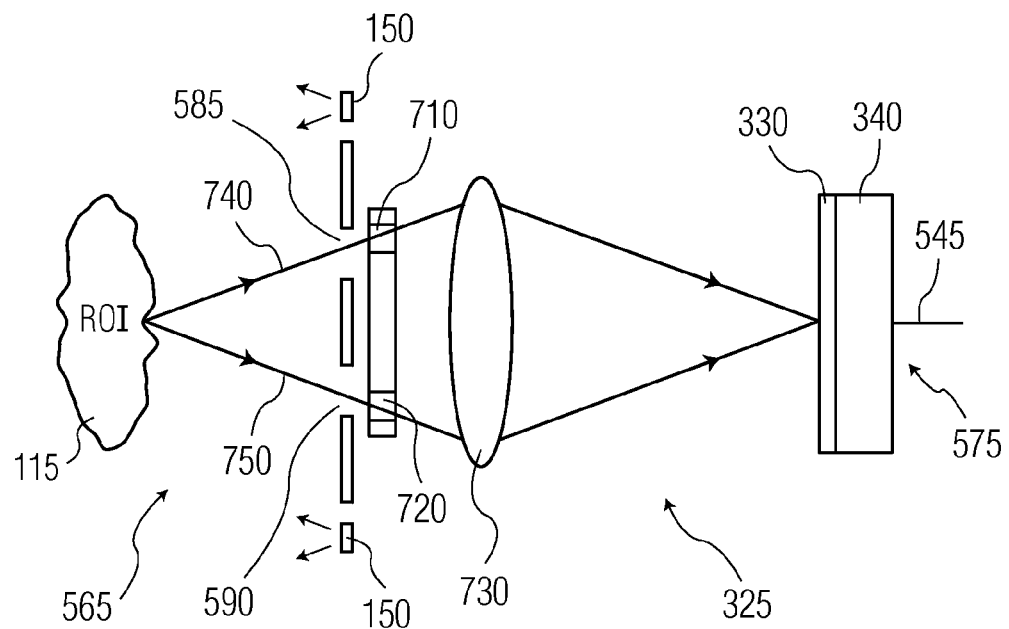
Figure 7B:
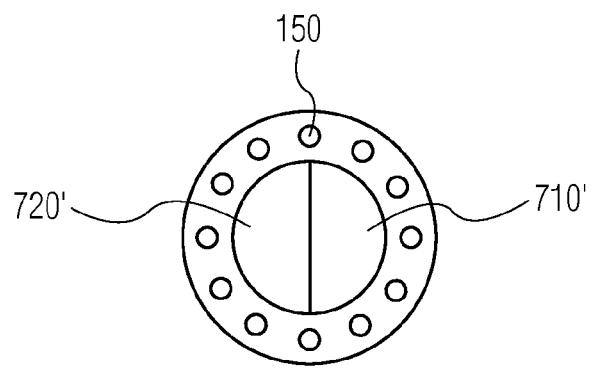
Figure 8:
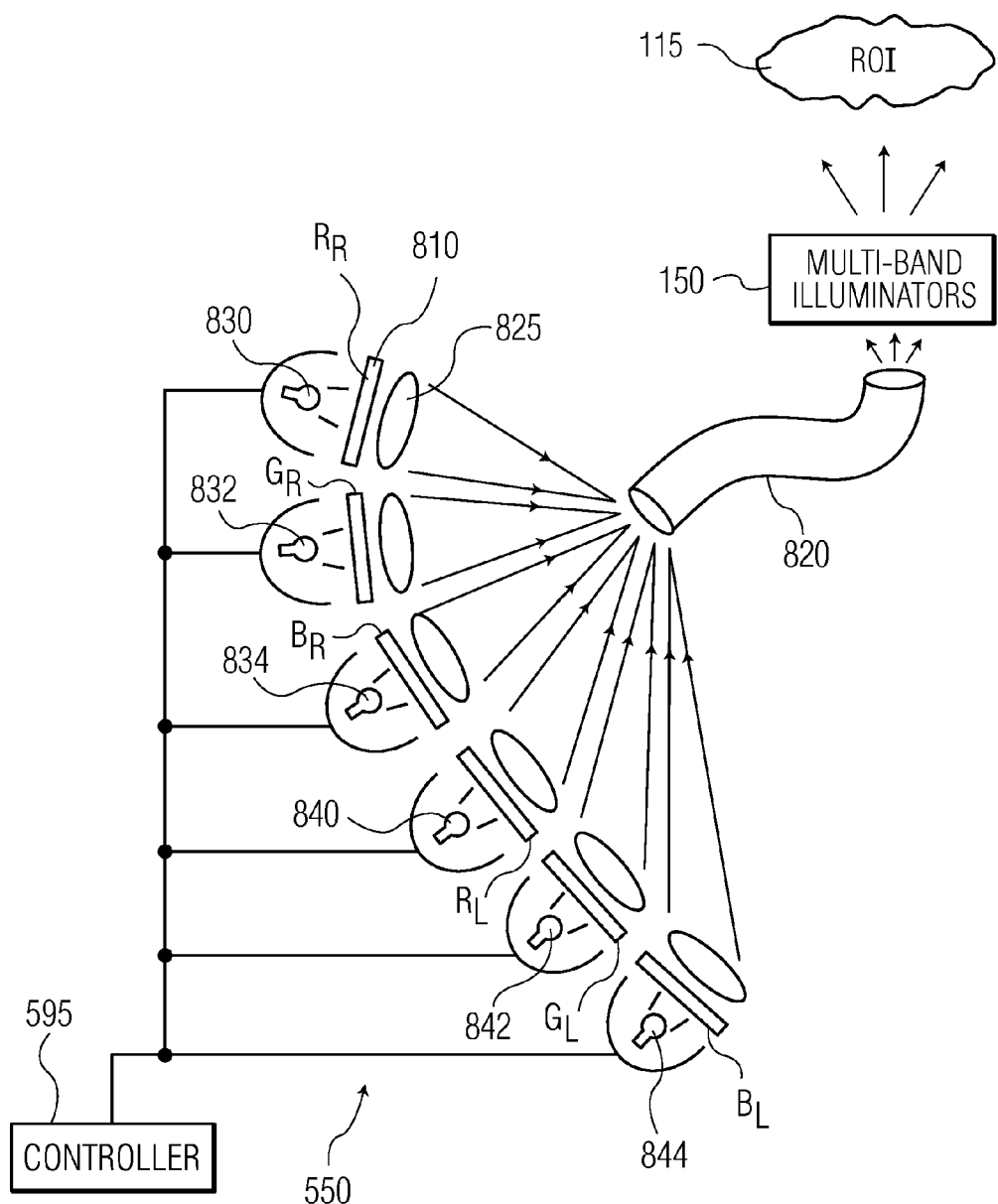
Figure 9:
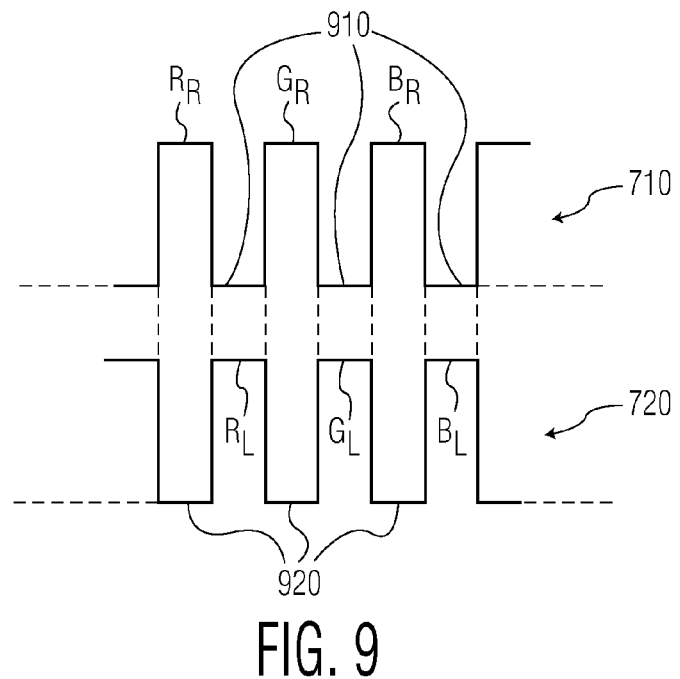
Figure 10A:
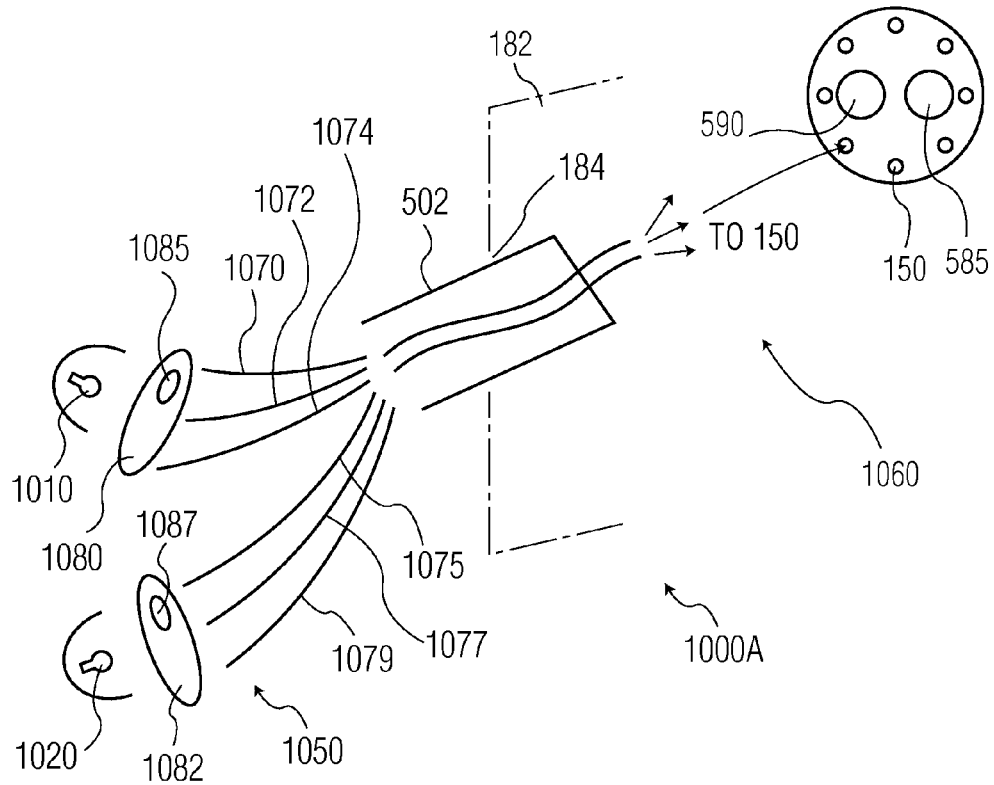
Figure 10B:
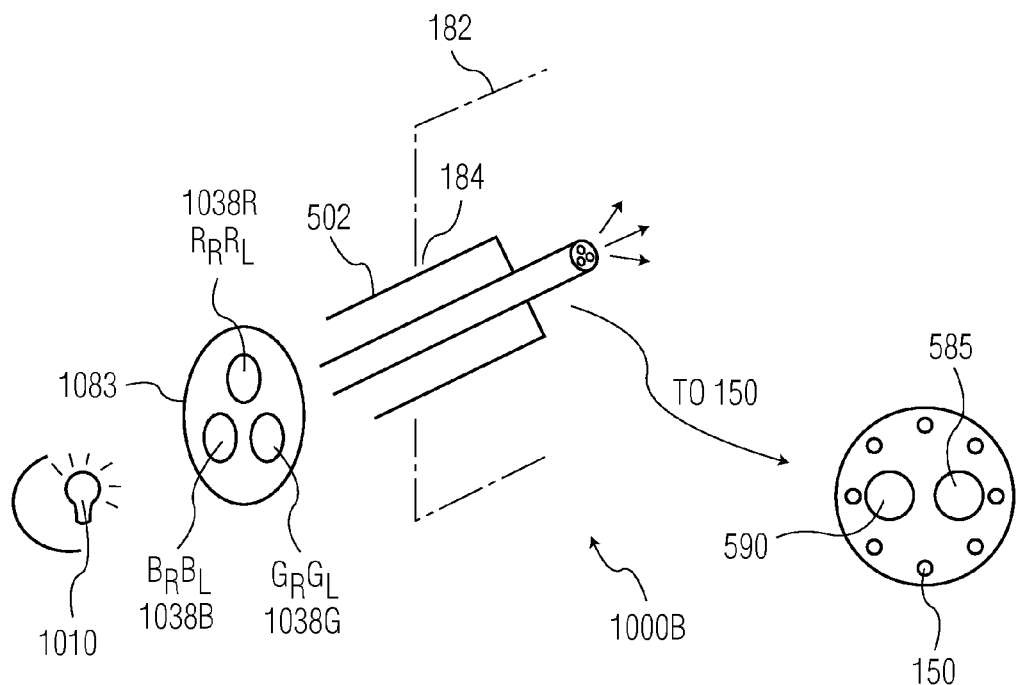
Figure 10C:
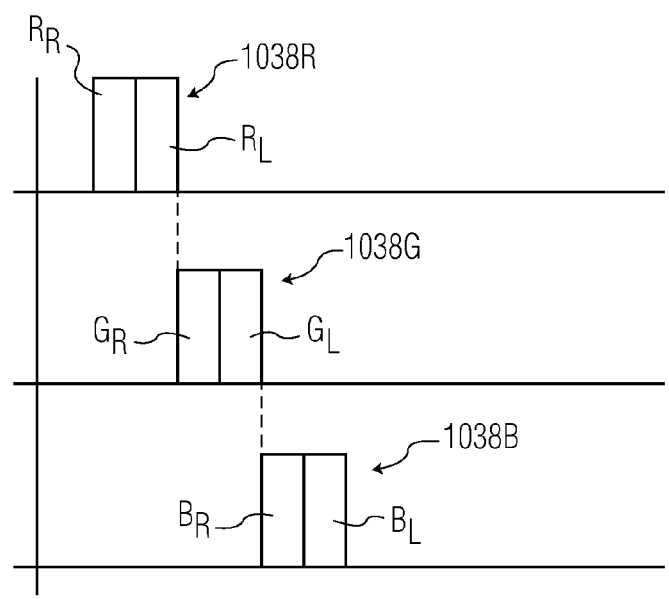
Figure 11A:
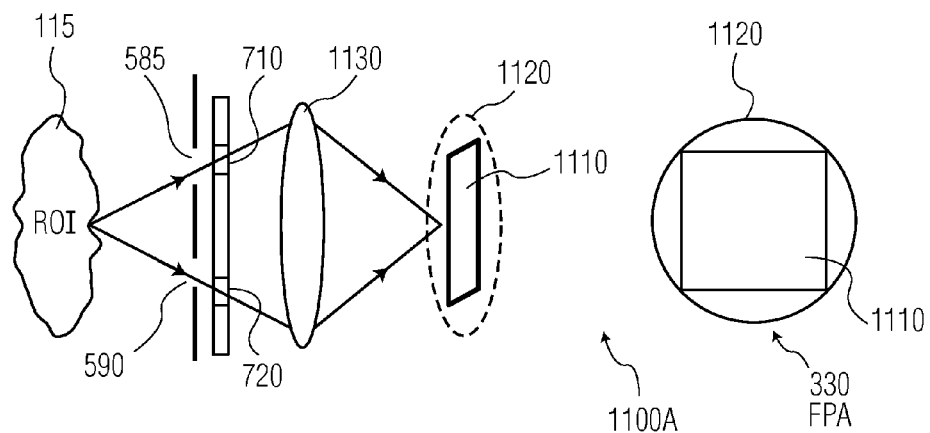
Figure 11B:
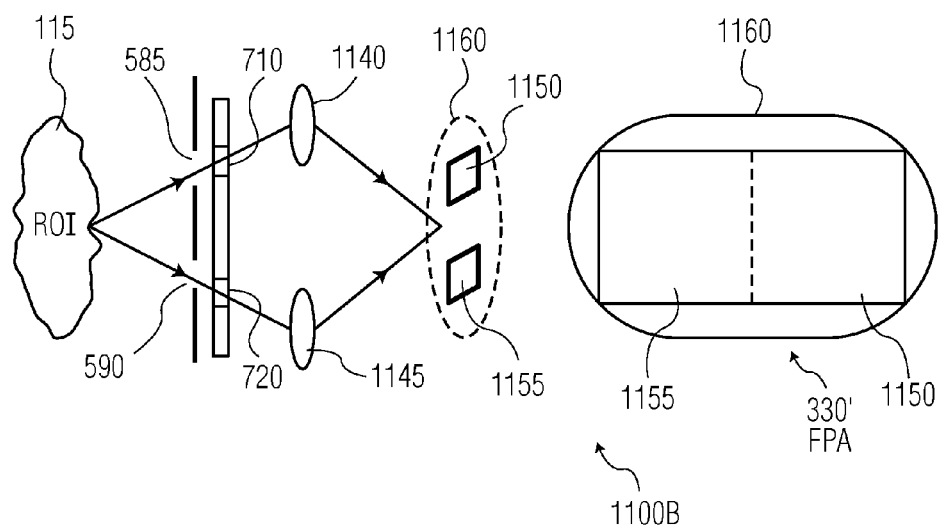
Figure 12A:
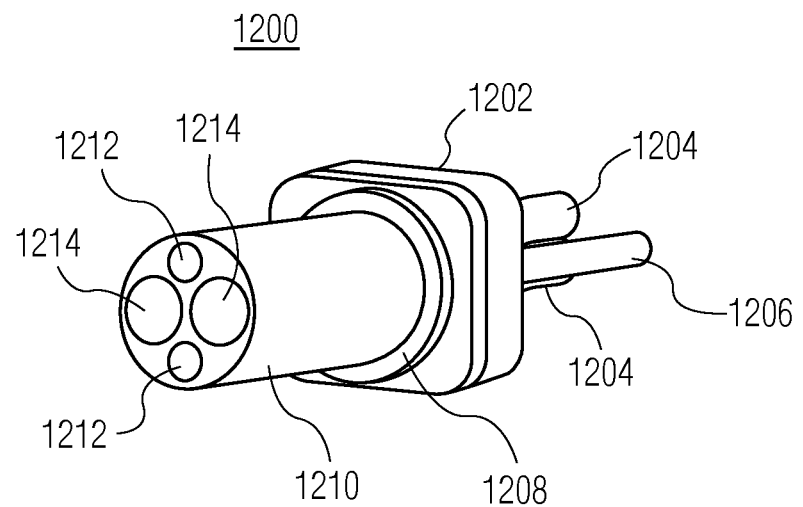
Figure 12B:
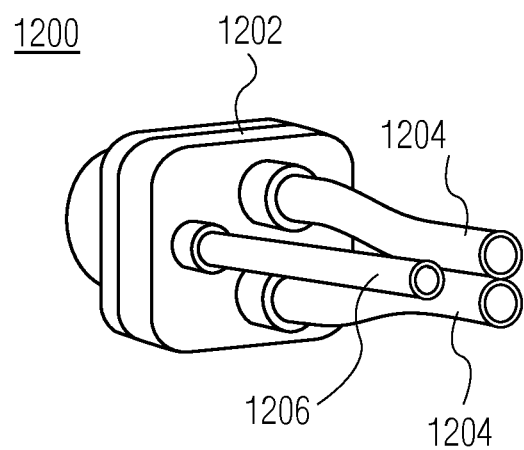
Figure 13:
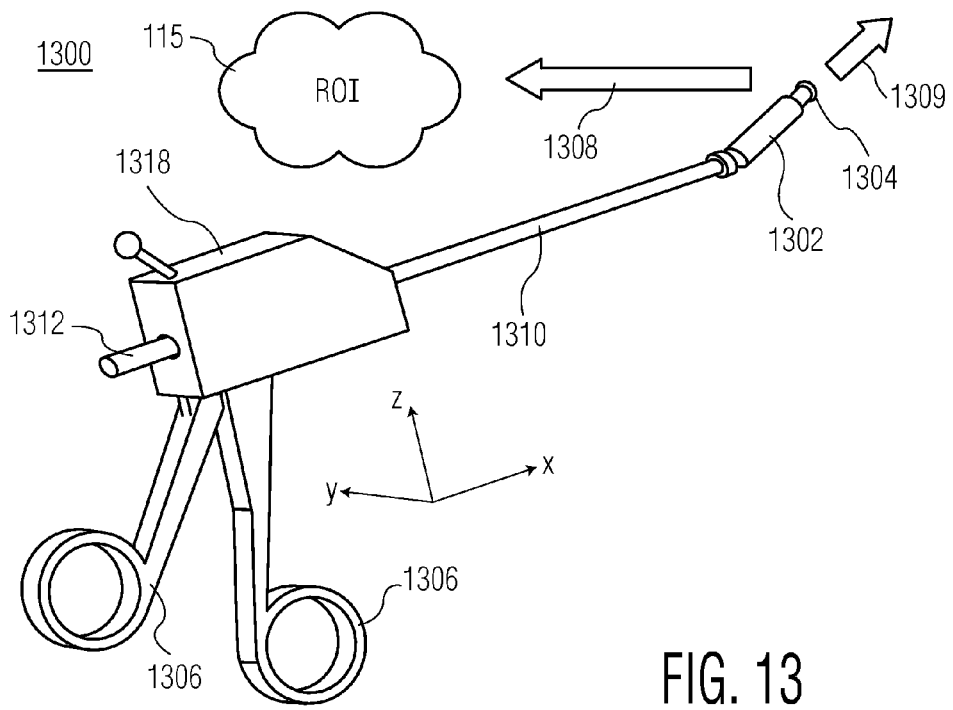
Figure 14:
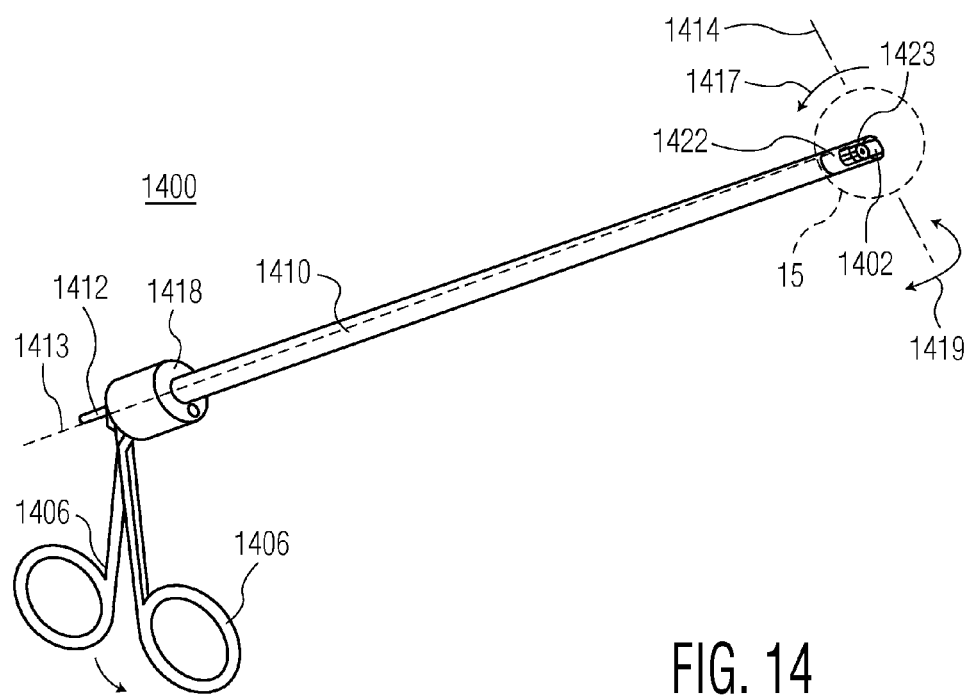
Figure 15:
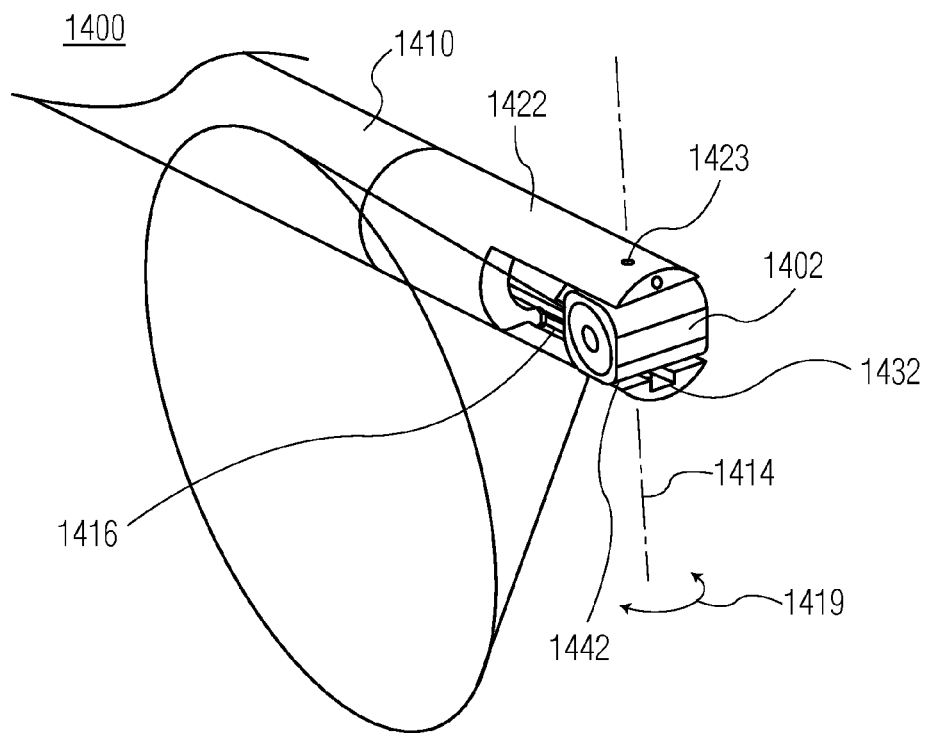
Figure 16:
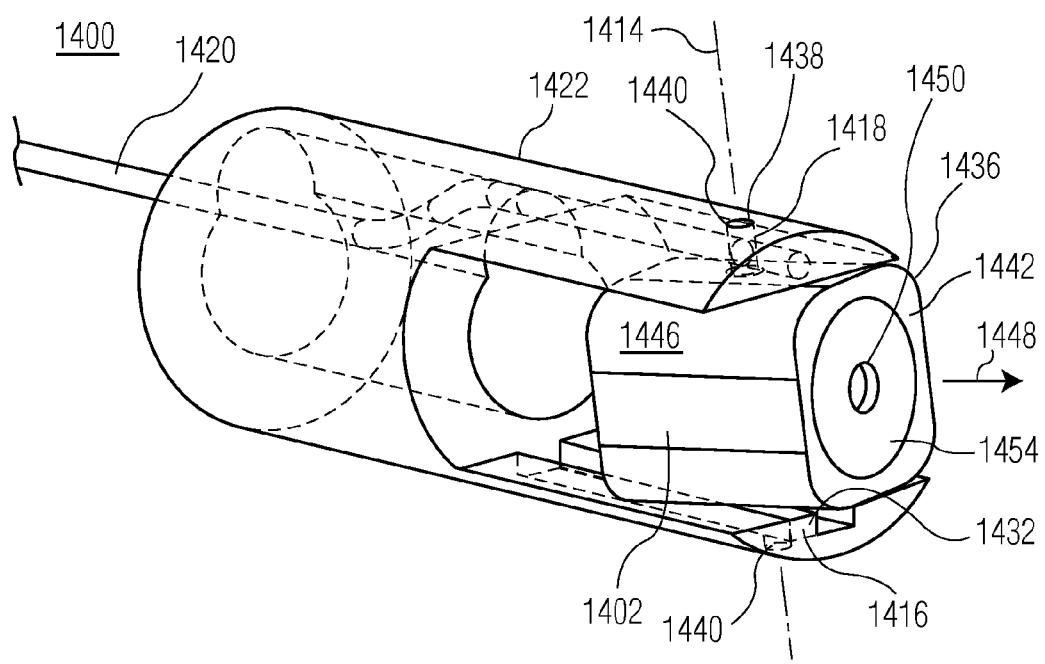
Figure 17:
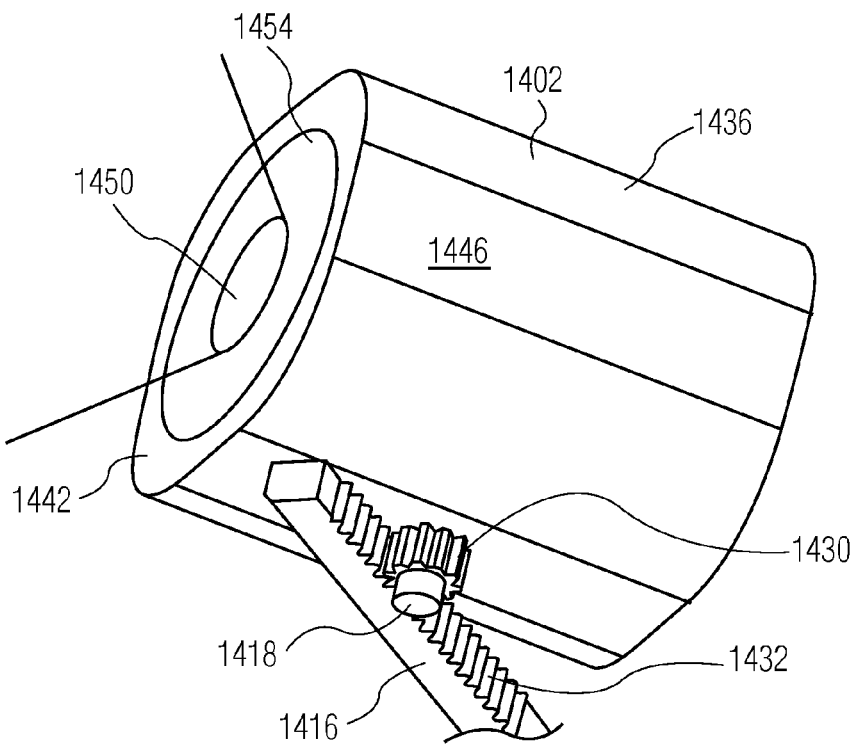
Figure 18A:
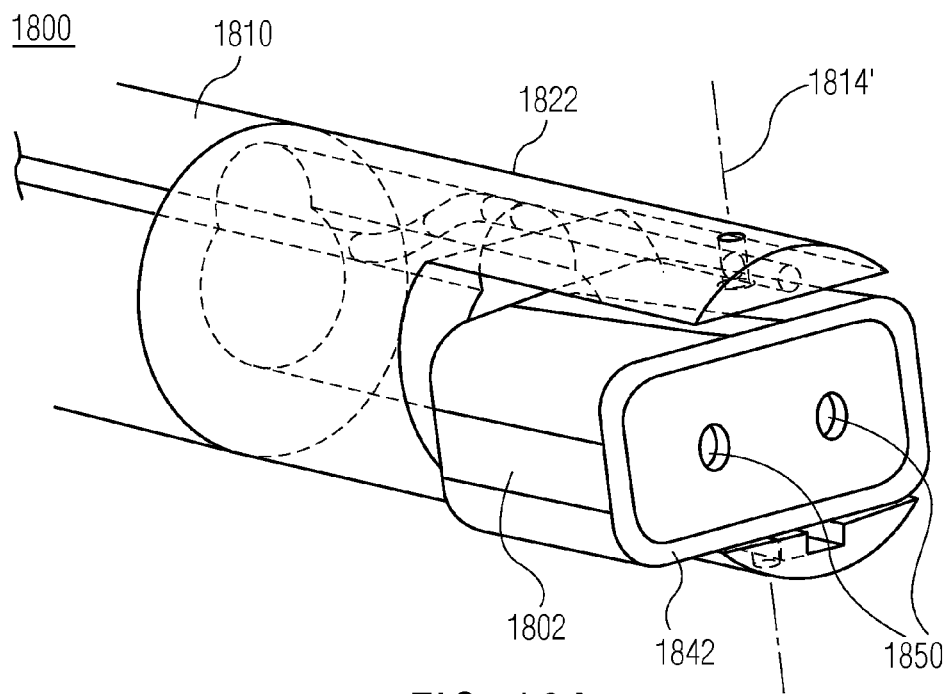
Figure 18B:
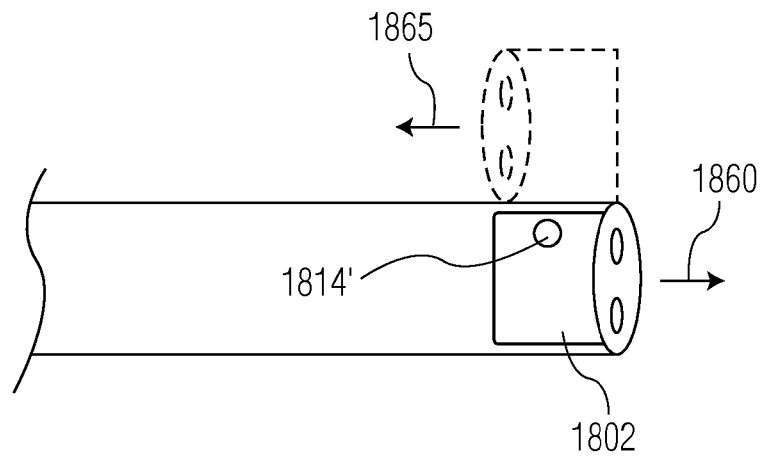
Figure 19:
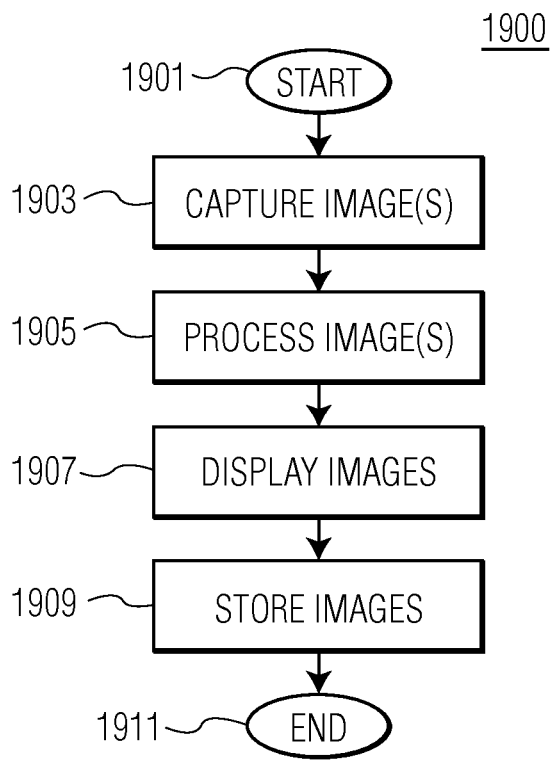
Figure 20:
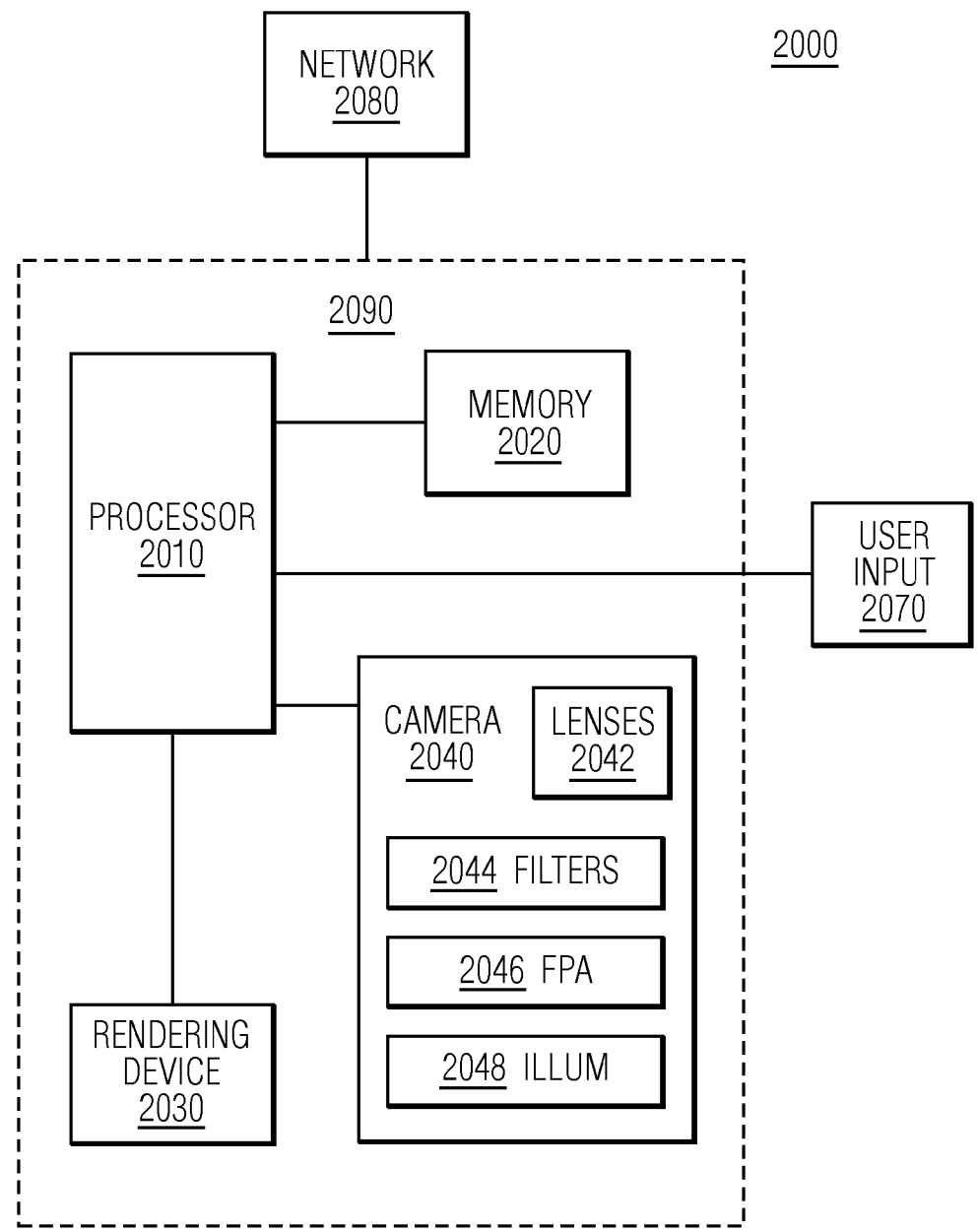

FIG. 4A which is a schematic view of an endoscope in accordance with an embodiment of the present system;

FIG. 4B is a front view of the endoscope in accordance with an embodiment of the present system;

FIG. 5 is a schematic view of an endoscope system in accordance with an embodiment or the present system;

FIG. 6 is a front view of the endoscope in accordance with an embodiment of the present system;

FIG. 7A is a schematic view of the imaging device components of the endoscope in accordance with an embodiment of the present system;

FIG. 7B is a front view of the endoscope showing semicircular right and left conjugated multi-bandpass filters (CMBFs) in accordance with an embodiment of the present system;

FIG. 8 is a schematic view of an illumination source of the endoscope in accordance with an embodiment of the present system;

FIG. 9 which is a graph illustrating pass and stop bands of a multi-band pass filter in accordance with an embodiment of the present system;

FIG. 10A is a schematic view of a system in accordance with an embodiment of the present system;

FIG. 10B is a schematic view of a system in accordance with an embodiment of the present system;

FIG. 10C which is a graph of colors passed through the first through third apertures in accordance with an embodiment of the present system;

FIG. 11A shows an imaging system having an endoscope with a single lens in accordance with an embodiment of the present system;

FIG. 11B shows an imaging system having an endoscope with a dual lens configuration in accordance with an embodiment of the present system;

FIG. 12A shows a front perspective view of a stereoscopic imaging system in accordance with an embodiment of the present system;

FIG. 12B shows a rear perspective view of a stereoscopic imaging system of FIG. 12A in accordance with an embodiment of the present system;

FIG. 13 illustrates a stereoscopic imaging device in accordance with an embodiment of the present system;

FIG. 14 illustrates an endoscope in accordance with an embodiment of the present system;

FIG. 15 is a detailed view of the distal end portion of the endoscope in accordance with an embodiment of the present system;

FIG. 16 is a detailed view of the distal end portion of the endoscope in accordance with an embodiment of the present system;

FIG. 17 is a detailed view of the camera portion of the endoscope in accordance with an embodiment of the present system;

FIGS. 18A-18B are detailed views of a distal end portion of an endoscope in accordance with an embodiment of the present system:

FIG. 19 shows a flow diagram that illustrates a process in accordance with an embodiment of the present system; and FIG. 20 shows a portion of a system (e.g., peer, server, etc.) in accordance with an embodiment of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well known devices, circuits, tools, techniques and methods are omitted so as not to obscure the description of the present system. It should be expressly understood that the drawings are included for illustrative purposes and do not represent the scope of the present system. In the accompanying drawings, like reference numbers in different drawings may designate similar elements.

As used herein, the term endoscope will refer to medical scopes for viewing an enclosed area such as, for example, laparoscopes, boroscopes, bronchoscopes, colonoscopes, choledoshoscopes, duodenoscopes, echoendoscopes, enteroscopes, esophagoschoes, gastrocopes, laryngoscopes, rhinolaryngoscopes, simoidoscopes, and/or other similar imaging apparatus. Further, it is envisioned that spectroscopic camera (e.g., imaging) portions described herein may be used in vehicles such as aircraft, space exploration, remote controlled (e.g., unmanned) rovers, robots, etc., in (e.g., space-, air-, land-, and/or underwater-based environments. Further, navigation systems may interface with the present system so as to provide remote navigation capabilities of these vehicles. The present system including spectroscopic 3D camera may be incorporated and/or coupled with the various aforementioned and other systems and miniature configurations to provide spectroscopic 3D images, including depth perception of the images captures by the spectroscopic 3D camera, e.g., for remote navigation, imaging, exploration and the like of objects including miniature objects and/or small crevices, openings, channels in the objects, which may be any type of body, whether human, animate, and/or inanimate.

For purposes of simplifying a description of the present system, the terms "operatively coupled", "coupled" and formatives thereof as utilized herein refer to a connection between devices and/or portions thereof that enables operation in accordance with the present system. For example, an operative coupling may include one or more of a wired connection and/or a wireless connection between two or more devices that enables a one and/or two-way communication path between the devices and/or portions thereof. For example, an operative coupling may include a wired and/or a wireless coupling to enable communication between a content server (e.g., a search engine, etc.) and one or more user devices. A further operative coupling, in accordance with an embodiment of the present system may include one or more couplings between two or more user devices, directly or via a network source, such as the content server.

The term rendering and formatives thereof as utilized herein refer to providing content, such as digital media which may include, for example, audio information, visual information, audiovisual information, etc., such that it may be perceived by at least one user sense, such as a sense of sight and/or a sense of hearing. For example, the present system may render a user interface (UI) on a display device so that it may be seen and interacted with by a user. Further, the present system may render audio visual content on both of a device that renders audible output (e.g., a speaker, such as a loudspeaker) and a device that renders visual output (e.g., a display). To simplify the following discussion, the term content and formatives thereof will be utilized and should be understood to include audio content, visual content, audio visual content, textual content and/or other content types, unless a particular content type is specifically intended, as may be readily appreciated.

The user interaction with and manipulation of the computer environment may be achieved using any of a variety of types of human-processor interface devices that are operationally coupled to a processor (e.g., a controller, a logic device, etc.) or processors controlling the display environment. The system may operate alone or in accordance with a user interface (UI) such as a graphical user interface (GUI) which may be rendered on a display of the system. The display may include a two- or three-dimensional display.

Stereoscopic endoscopes according to the present systems include Conjugated Multi-Bandpass Filters (CMBFs) integrated with and/or covering one or more objective lenses (at the distal end of single and/or multiple bores) to project and form sub-images directly on a single Focal Plane Array (FPA) without using lenticular lens arrays and/or relay lenses typically used to form images on an imager and/or to relay optical images to an eyepiece at the proximal end of conventional endoscopes. Optical sub-images, captured by the FPA at the distal end of the endoscopes according to the present systems, are processed to form 3D images and/or sub-image data/information, such as by converting optical images and/or sub-images to digital form, e.g., by an analog-to-digital (A/D) converter for processing by a processor, e.g., to form 3D image data from (e.g., 3 or 6) sets of sub-image data.

Unlike conventional endoscopes and boroscopes, endoscopes in accordance with embodiments of the present system dispense with the need for a lenticular lens portion, and project right and left images directly on a single FPA without any lenticular lens portion. Accordingly, endoscopes in accordance with the present system provide images from the objective lens system to the FPA without the need for a lenticular lens or lens array. Further, both the objective lens system and the FPA may be located at a distal end of the endoscope and may be inserted inside a body for viewing a region of interest. Integrated circuitry formed on/in a semiconductor substrate such as an Integrated Silicon on Chip (ISOC) substrate may also be included at, for example, the distal end of the endoscope.

Figure 1A:
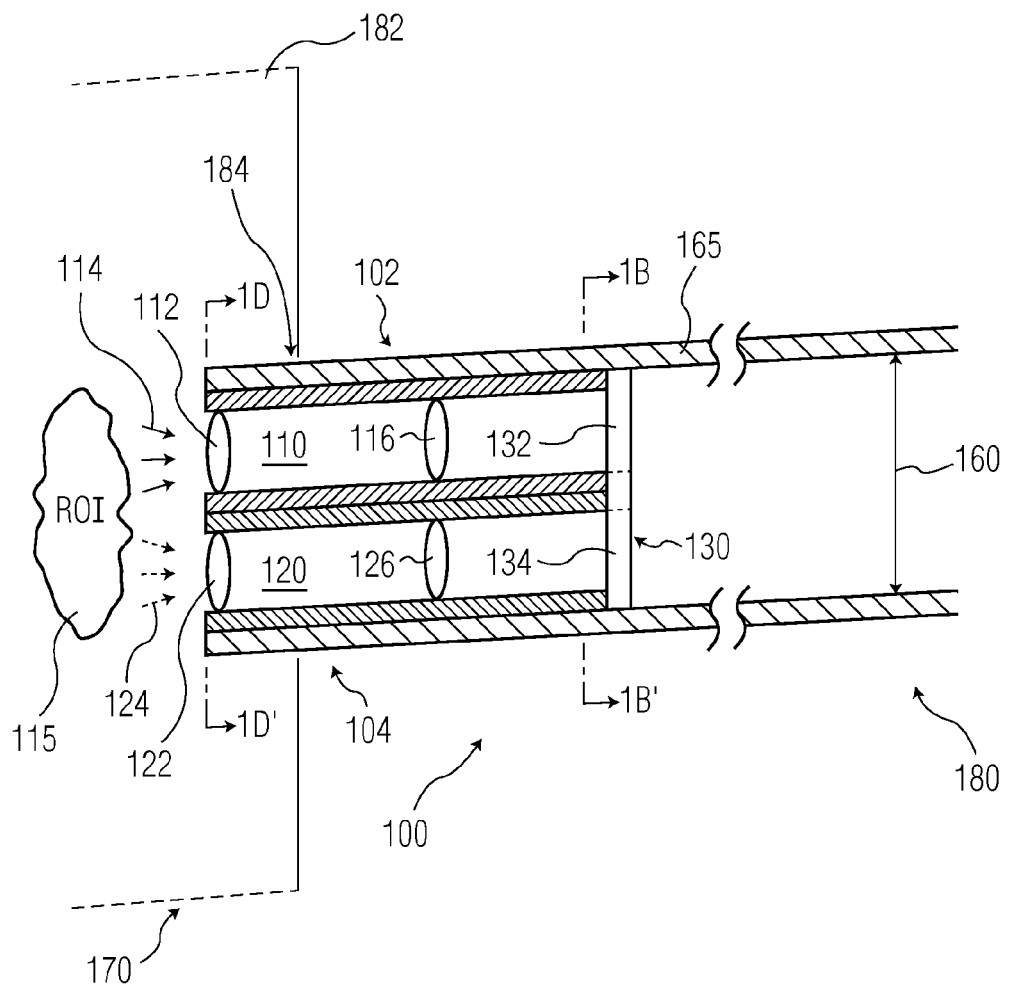
FIG. 1A is a side cross sectional view of a dual-objective endoscope in accordance with an embodiment of the present system.

FIG. 1A is a side cross sectional view of a dual-objective endoscope 100 in accordance with an embodiment of the present system. The endoscope 100 may include first and second sub-units 102 and 104, respectively, which may be identical to each other and may be situated adjacent to each other. The first sub-unit 102 may carry a right image and the second sub-unit 104 may carry a left image. As shown in FIG. 1A, the dual objective endoscope 100 comprises a first bore 110 having a first lens 112 for receiving first image rays 114 from an ROI 115; and a second bore 120 having a second lens 122 for receiving second image rays 124 from the ROI 115. The first and second lenses 112, 122 may each include several lenses, such as an objective lens (112, 122) for collecting the image rays 114, 124, a focusing lens (116, 126) to focus the collected image rays 114, 124 on a single Focal Plane Array (FPA) 130. Light sources or illuminators 150 (FIG. 1D) may sequentially illuminate the region of interest 115 with different colored lights, such as red, green and blue lights. The first sub-unit 102 may be located in the first bore 110 and the second sub-unit 104 may be located in the second bore 120. The first and second bores 110, 120 may be located in a main bore 160 of a body 165 having a distal end 170 and a proximal end 180. Accordingly, portions of endoscopes which carry/project the right image may be known as a right image channel and those portions of the endoscope which carry/project the left image may be known as a left image channel. During use, the distal end 170 of the endoscope 100 is typically inserted within a body 182 through a cavity or opening 184 of a body 170 while the proximal end 180 remains outside of the body 105. The body 170 may be that of a patient, human or otherwise, as well as the body of any inanimate object where it is desired to look inside the object.

The lenses 112, 122 may simultaneously receive light reflected from the region of interest 115 for simultaneously imaging the first/right and second/left image rays 114, 124 on different (right and left) areas 132, 134, respectively, of the FPA 130. When the time-sequential illumination provides RGB light one at a time, after three sequences, a full color image is collected on the FPA 130. For example, three (e.g., RGB) right images may be sequentially superimposed on the right area 132, and simultaneously three (RGB) left images may be sequentially superimposed on the left area 134, as described in connection with FIGS. 1B-1D. Accordingly, in the present embodiment, three images may be captured to form a full color image. However, in embodiments which include a shutter, such as is described below in connection with FIGS. 7A-7B, six images may be necessary to obtain a full color image.

Figure 1B:
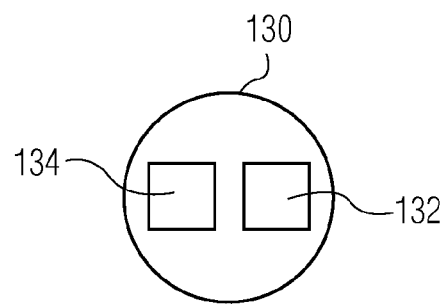
FIG. 1B is a view of the endoscope taken along lines 1B-1B' of FIG. 1A showing a front view of the FPA.
Figure 1C:
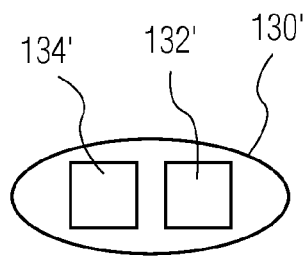
FIG. 1C shows a front view of an FPA in accordance with an embodiment of the present system.

FIG. 1B is a view of the endoscope 100 taken along line 1B-1B' of FIG. 1A showing a front view of the FPA 130. The right image area 132 of the FPA 130 captures the first/right image rays (projection) 114 and the left image area 134 of the FPA 130 captures the second/left image rays (projection) 124. Although a round FPA 130 and square image areas 132, 134 are shown, it is envisioned that the FPA 130 and image areas 132, 134 may include other shapes and/or sizes, such as an oval and/or a rectangular shape type, etc., where the FPA 130 and the image areas 132, 134 may have the same or different shape types. For example, FIG. 1C shows a front view of an oval FPA 130' in accordance with another embodiment of the present system. The FPA 130' includes square (or round or any desired shape) right image area 132' and left image area 134' which correspond with the right image area 132 and the left image area 134, respectively, of the FPA 130 shown in FIG. 1B.

Figure 1D:
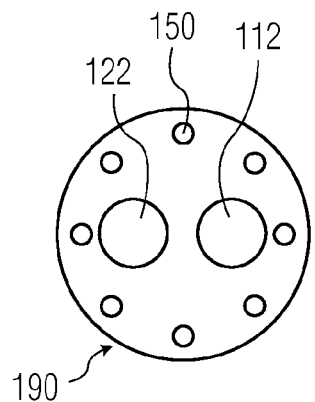
FIG. 1D is a front view of the endoscope in accordance with an embodiment of the present system.

FIG. 1D is a front view of the endoscope 100 along line 1D-1D' of FIG. 1A showing an imaging unit 190 that includes the right objective lens 112, and the left objective lens 122, where both lenses 112, 114 simultaneously receive light emitted from illuminators 150 and reflected from the ROI 405. The illuminators 150 may be arranged around the periphery of the imaging unit 190 and may be configured (e.g., under the control of a controller or processor) to sequentially provide different light of different wavelengths and therefore colors (e.g., corresponding with an RGB spectrum) one at a time. For example, at time t1, the illuminators 150 may provide red light, in response to which red right and left images may be captured simultaneously on the right image area 132 and the left image area 134 of the FPA 130 (shown in FIG. 1A-1B). Then, at a later time such as at time t2, the illuminators 150 may provide green light, and green right and left images may be captured simultaneously on the right image area 132 and the left image area 134 of the FPA 130. Then, at yet a later time such as t3, the illuminators 150 may provide blue light and blue right and left images may be captured simultaneously on the right image area 132 and the left image area 134 of the FPA 130.

The system may then superimpose information related to the captured green and blue right and left images (e.g., captured at times t2 and t3) upon the captured red right and left images (e.g., captured at time t1) so as to form a full color three dimensional images which may be displayed on a display of the system. Accordingly, after time t3, that is after three sequences of illumination (e.g., of red, green, and blue light), a full color image may be captured by the right and left image areas 132 and 134, respectively, for further processing by an Integrated Silicon on Chip (ISOC). Accordingly, three images from each of the right and left image areas 132 and 134, respectively, of the FPA 130 may be processed to form a full color image, where a right image is formed on a right image area 132 of the FPA 130, and a left image is formed on a left image area 134 of the FPA 130. A processor may be configured to correlate and combine the three right and left images to form a stereo and/or 3D image.

Figure 2A:
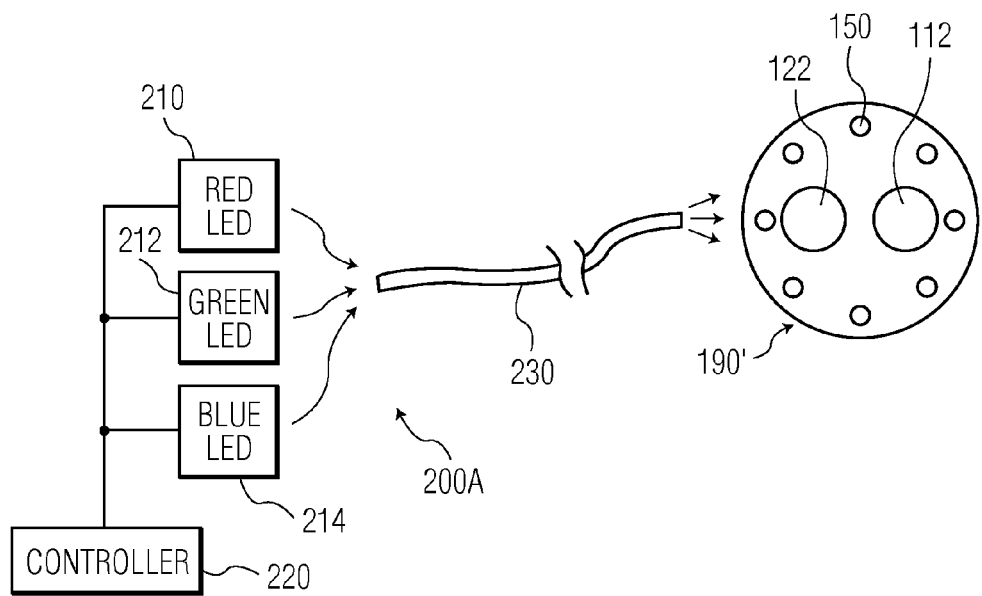
FIG. 2A is a schematic view of a system using an LED light source in accordance with an embodiment of the present system.

The sequential illumination with red, green, and blue light (e.g., one at a time), may be provided using any suitable light source such as by light emitting diodes (LEDs), xenon sources, etc. For example, FIG. 2A is a schematic view of a system 200A using an LED light source in accordance with an embodiment of the present system. The system 200A may include an endoscope (e.g., such as an endoscope viewed from the front having an imaging unit 190'), red, green, and blue LEDs 210, 212, and 214, respectively, which may provide corresponding light (e.g., red, green, and blue) to an illuminator 150 of the imaging unit 190' via a light channel 230. The light channel 230 may include any suitable light conducting channel such as a fiber optic light channel, an acrylic light channel, etc.

In one embodiment, the light channel 230 comprises one or more fiber optics to directly illuminate the ROI 15 from light exiting through the distal or exit end(s) of the fiber optics(s), such as through the illuminators 150 shown in the various figures of the various embodiments, such as FIGS. 1D, 2A-2C, 5-8, and 10A-10B, for example. In another embodiment instead of direct illumination, one or more interface units, such as one or more periscopes to be described in connection with FIG. 16, may receive light from the distal end(s) of the light guide(s), e.g., at least one fiber optic cable. The periscope(s) directs, e.g., reflects, light into a light exit unit which is located around the right and left pupils and directs light out to illuminate the ROI 115.

The light channel 230 may also include a coupler portion which may couple the LED 210, 212, and/or 214 to the light channel 230 and a decoupler portion which may couple the light channel 230 to the illuminator 150. The LEDs 210, 212, and/or 214 may emit monochromatic light and may be sequentially turned on one at a time under the control of a controller 220. The controller 220 and/or the LEDs 210, 212, and/or 214 may be located at, or connected to, a proximal end 180 (FIG. 1A) of the endoscope 100, for example, such that the light provided by the LEDs may be transmitted through light guide(s) or light channel(s) 230 such as fiber optic(s), to the illuminators 150 of the imaging unit 190' at the distal end of the endoscope 100.

Figure 2B:
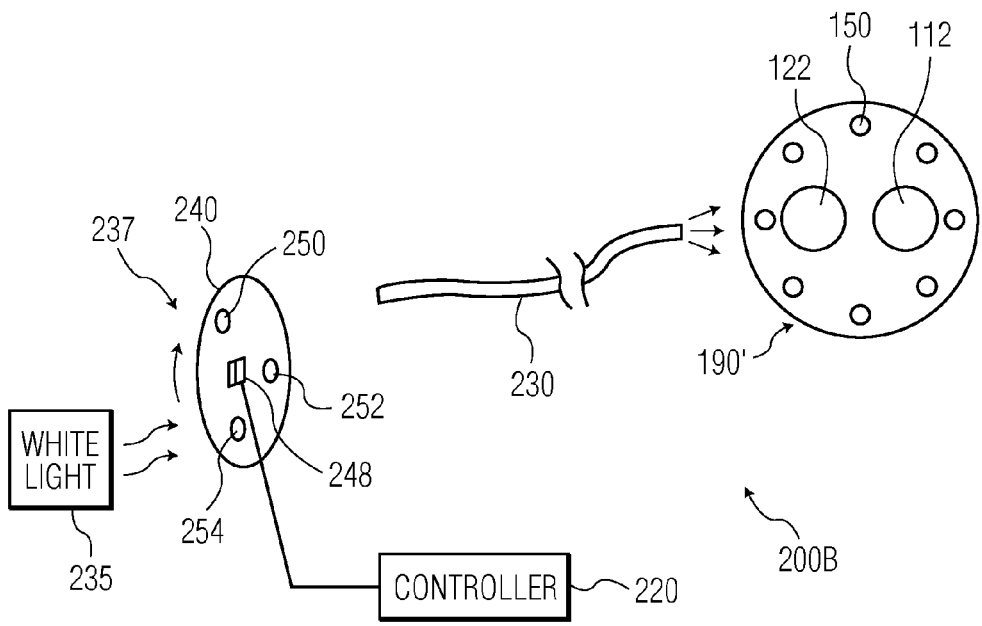
FIG. 2B is a schematic view of a system using a white light source in accordance with an embodiment of the present system.

FIG. 2B is a schematic view of a system 200B using a white light source 235 in accordance with another embodiment of the present system. The white light source 235 may include a suitable light source emitting light which corresponds with a desired spectrum or spectrums such as a white spectrum. A filter such as a filter 237 may be included to pass only desired wavelengths (or frequencies, etc.) of light under the controller 220. The filter 237 may include a solid state and/or analog filter. For example, the filter 237 may include a rotating color wheel 240 that has three openings covered with red, green and blue filters 250, 252, 254, respectively. As the color wheel 240 is rotated (e.g., by a motor 248 such as a stepper motor under the control of the controller 220 at a desired rotational frequency ($\omega$)), such that the filter may sequentially pass a single color of light to the illuminators 150 via the light channel 230 at a time.

Figure 2C:
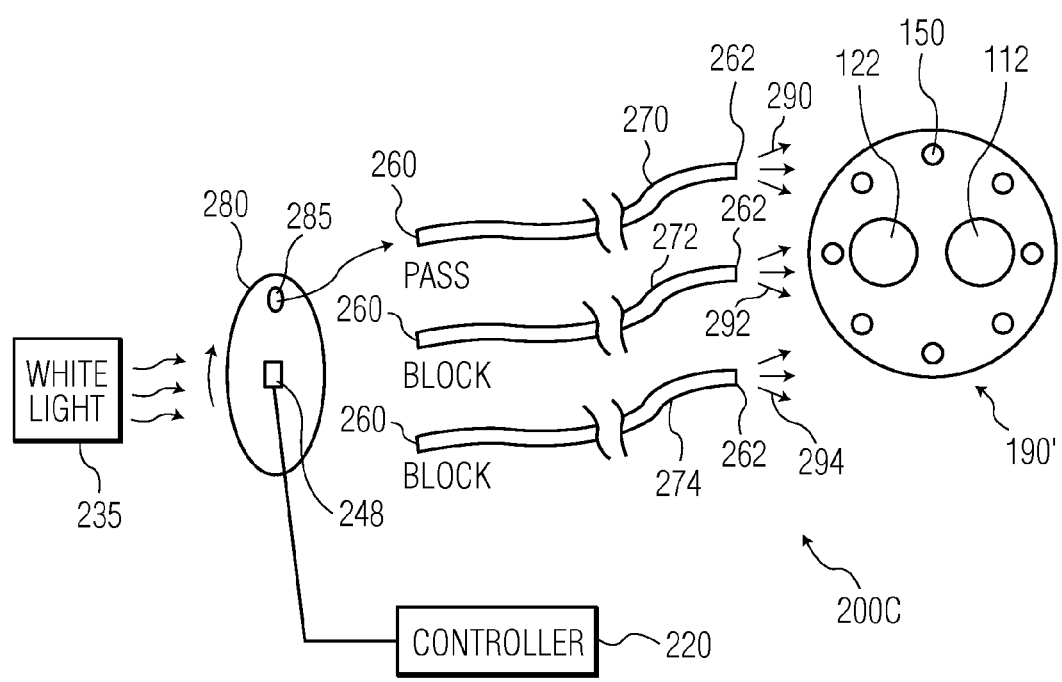
FIG. 2C is a schematic view of a system using a white light source in accordance with an embodiment of the present system.

FIG. 2C is a schematic view of a system 200C using a white light source 235 in accordance with an embodiment of the present system. The system 200C may be similar to the system 200B. However, the system 200C may include a rotating wheel 280 which may include a single opening (as opposed to the three openings of the rotating wheel 240 of system 200B) and filtered light channels (270, 272, and 274). The filtered light channels 270, 272, 274 may pass only desired wavelengths of light such as wavelengths of light which correspond with red, green, and blue light spectrums, respectively (and therefore block other wavelengths of light). It is further, envisioned that the rotating wheel 280 may include a plurality of openings. During operation, the light may pass from the white light source 235 through the opening to a single one of the filtered light channels 270, 272, 274. Thus, color filters are associated with the light channels, such as provided at entrance and/or exit faces 260, 262 of each of the light channels 270, 272, 274. In this case, three light channels 270, 272, 274 are provided, one having a red filter, a second channel having a green filter and the third light channel having a blue filter. The rotating wheel 280 has one opening 285 that allows white light from a white light source 235 to pass to one channel when the opening is aligned with the channel or light guide. As the rotating wheel 280 rotates, the opening 285 sequentially allows white light to enter the entrance faces on one channel at a time. In FIG. 2C, the opening 285 is aligned with the red channel 270 so that red light 290 is provided to the illuminators 150 at the distal end of the endoscope. At a later time, such as time t2, when the wheel 280 rotates and the opening is aligned with the green channel 272, then green light 292 is provided to the illuminators 150 and so on, where similarly at a later time t3 when the wheel 280 rotates and the opening is aligned with the blue channel 274, then blue light 294 is provided to the illuminators 150 for illuminating the ROI sequentially with red, green and blue lights 290, 292, 294.

In summary, the FPA 130 of an endoscope in accordance with an embodiment of the present system may simultaneously capture right and left optical images directly received (e.g., one color at a time) from an objective lens system of the endoscope and convert right and left optical images (via an analog-to-digital converter (A/D)) to digital signals which may then be processed by an Integrated Silicon on Chip (ISOC). That is, at time t1, both right and left red images (e.g., of an ROI) are simultaneously imaged on the right and left areas 132, 134 of the FPA 130 (FIGS. 1A-1B); at time t2, both right and left green images are simultaneously imaged on the right and left areas 132, 134 of the FPA 130; and at time t3, both right and left blue images are simultaneously imaged on the right and left areas 132, 134 of the FPA 130.

The various illumination schemes and system shown in FIG. 2A-2C may be used with various embodiments of the present endoscopes and/or systems, and different combinations thereof, such as single and/or double bore endoscopes, using mono and/or color FPA, to form sub-images on the entire or sub-portions of the FPA, for example.

Figure 3A:
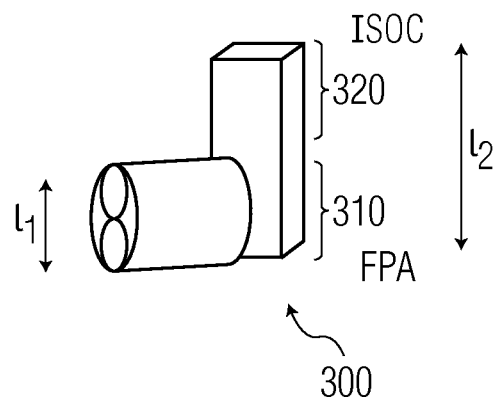
FIG. 3A is a perspective view of an imaging unit accordance with an embodiment of the present system.
Figure 3B:
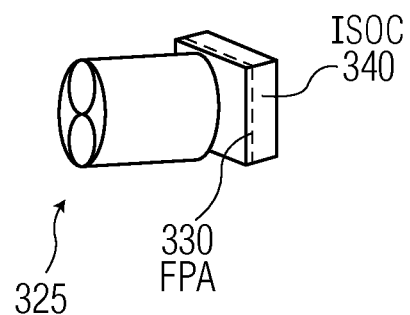
FIG. 3B is a perspective view of a compact imaging unit in accordance with an embodiment of the present system.

FIG. 3A is a perspective view of an imaging unit 300 in accordance with an embodiment of the present system. The imaging unit 300 may include one or more of an FPA 310 and an Integrated Silicon on Chip (ISOC) 320 which are formed on the same surface of a semiconductor substrate adjacent to where the FPA 310. Unfortunately, by placing the ISOC 320 next to the imager/FPA 310 (i.e., on the same surface of a substrate) the footprint of the imaging unit 300 is increased (e.g., from length $l_1$=4 mm to $l_2$=6.5 mm or more). This may increase a diameter of a corresponding endoscope, which may not be desirable, as a larger incision or opening (e.g., see, 184, FIG. 1A) in the body (e.g., see, 182, FIG. 1A) is required for insertion of the endoscope through the opening (e.g., 184, FIG. 1A). A compact imaging unit is shown in FIG. 3B. In particular, FIG. 3B is a perspective view of a compact imaging unit 325 in accordance with another embodiment of the present system. The imaging unit 325 may include an FPA 330 on a first side of a substrate and an ISOC 340 on an opposite side of the substrate. Accordingly, the imaging device 325 may have a footprint which is substantially identical to a footprint of the single FPA 330 where the ISOC 340 is on opposite side of the substrate of the FPA 330. The imaging unit 325 may be referred to as a folded imager 325.

Figure 3C:
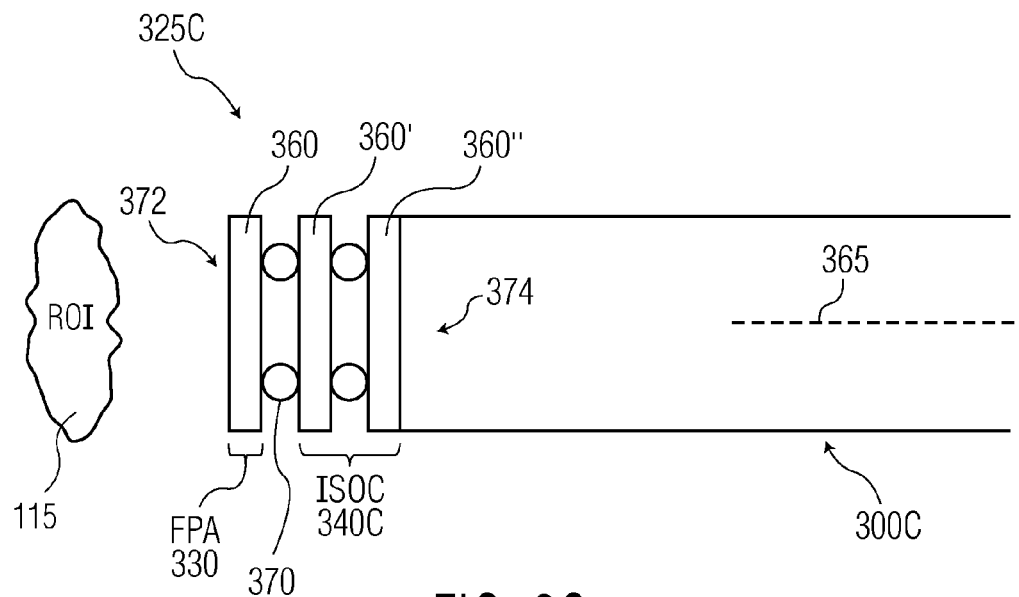
FIG. 3C is a schematic view of an endoscope including an imaging device having a folded imager in accordance with an embodiment of the present system.

FIG. 3C is a schematic view of an endoscope 300C including an imaging device having a folded imager 325C in accordance with an embodiment of the present system for capturing images from the ROI 115. The folded imager 325C may be formed from stacked layers 360, 360', 360" stacked axially along a longitudinal axis 365 of the endoscope 300C. The imaging device 325C may include a single FPA 330 at a front end 372 and the processing circuits (e.g., including an ISOC) 340C formed on at least one layer stacked at a back end 374 of the imaging device 325C (which may be similar to the imaging device 325 shown in FIG. 3B) over the single FPA 330. The ISOC stack(s) 340C may be connected to the single FPA 330 through connection bumps 370.

Figure 3D:
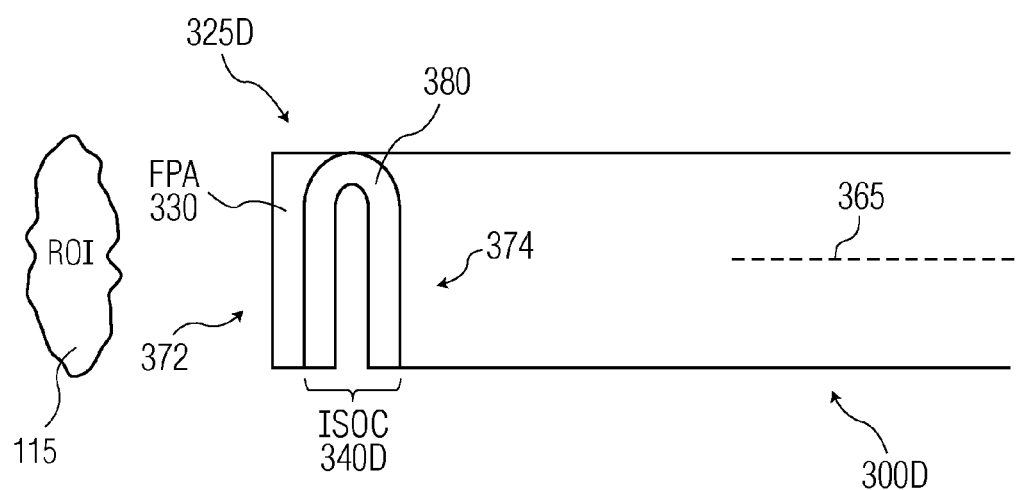
FIG. 3D is a schematic view of an endoscope including an alternative imaging device in accordance with an embodiment of the present system.

FIG. 3D is a schematic view of an endoscope 300D including an alternative imaging device 325D in accordance with an embodiment of the present system for capturing images from the ROI 115. Instead of stacks connected by bumps 370 of the imaging device 325C (of FIG. 3C), the imaging device 325D may include a folded substrate 380 having the single FPA 330 at the front end 672 and the ISOC 340D at the back end 374 of the imaging device 325D. The folded flexible substrate 380 may be formed from patterned silicon membrane or flexible printed circuit boards, or other suitable material.

The optical images captured by the FPA 330 (i.e., directly received from the objective lens system) are converted (by an A/D) to digital signals (e.g., digital image information) which may be processed by an image processor such as the ISOC 340 located behind the FPA 330. The ISOC 340 processes the digital signals (i.e., the digital image information representing the optical images captured by the FPA 330) and outputs video signals which are transmitted (e.g., using a wired or wireless communication method) to a display screen of the system for viewing of 3D/stereo images of the ROI 115 (FIG. 1A) by a user (e.g., a surgeon, etc.). The system may also record 3D image information corresponding with the images for later use and/or may transmit the 3D image information to one or more locations for remote viewing (e.g., by a remote surgeon, etc.).

Another embodiment of the present invention uses a split pupil having right and left pupils. To achieve stereo vision or three dimensional vision (3D), different right and left images may be captured by the FPA and processed to form a 3D image. In some of the previous embodiment, both the right and left portions of the FPA (or right and left pupils) (e.g., corresponding with right and left image channels, respectively) receive light/images simultaneously. However, in embodiments where each image channel has its own bore (e.g., 110, 120) as shown in FIG. 1A, different right and left images received by the right and left pupils or lenses 112 and 122, respectively, are imaged on different areas 132, 134 of the FPA 130, as shown in FIG. 1B, thus providing stereoscopic image information which may be processed to form a 3D image.

In other embodiments, instead of having both right and left pupils/lenses receive images simultaneously, various schemes may be provided such that an image captured by the endoscope is only passes through a single pupil at any one time. For example, Conjugated Multi-Bandpass Filters (CMBFs) may be provided to cover, or be integrated with, the right and left pupils which may be formed by a single lens having right and left pupil portions, or two dedicated lenses, one lens for the right pupil and one lens for the left pupil, for use in single and/or dual bore endoscopes. Instead of CMBFs located over, or integrated with, the right and left pupil, switchable liquid crystal (LC) shutters or mechanical shutters may be controlled by a controller such that only one pupil passes image light reflected from the ROI at any one time to project the passed image light over substantially the entire area of the FPA, thus increasing resolution as compared to projecting images on only a portion of the FPA, where a processor construct a 3D image from six sequential sub-images ($R_R$, $G_L$, $B_R$, and BO, each projected over the entire FPA area. Of course, if desired, right and left images may be simultaneously projected over right and left portions of the FPA, resulting in reduced resolution, however, faster acquisition time for forming a 3D image, since the 3D image in this case is constructed by the processor from three (instead of six) sequential projections of simultaneous right and left sub-images ($R_R$ $R_L$, $G_R$ $G_L$, and $B_R$ $B_L$). For example, the controller and/or processor may vary a voltage applied to right and left LC shutters located over the right and left pupils, such that one LC shutter is open/transparent to pass the image light, and the other LC shutter is closed or not transparent to block the image light from passing through the other shutter. Alternatively, a controller may control movement of a mechanical shutter, as shown in FIGS. 4A-4B.

In particular, FIG. 4A shows a schematic view of an endoscope system 400 in accordance with another embodiment of the present system. The endoscope system 400 includes one or more of a controller 410, a micro-electro-mechanical (MEMS) shutter 415 for allowing time multiplexing of sub-images, an illumination portion 420, 420', a lens portion 425, and an FPA 430. The illumination portion 750 may include a light source, e.g., an external white light source in case the FPA is a color FPA having a color filter, or a light source(s) that provides different colors of light sequentially, e.g., Red (R), Green (G), and Blue (B) light. Optical guides may also be provided to direct the external light form the proximal end to a distal end of the endoscope where the light is then directed away from the endoscope to illuminate an ROI 115. Of course colored light source(s) may also be used with a monochrome FPA, where each color sequentially illuminates the ROI 115. The lens portion 425 may include one or more lenses which may project a right or left image of the ROI 115 upon the FPA 430 depending upon settings of the shutter 415 as will be discussed below. The shutter 415 may include a right shutter opening (or pupil) 440 and a left shutter opening (or pupil) 445 which may block or allow light to pass therethrough based upon a control signal from the controller 410. Accordingly, the right and left shutter openings (pupils) 440, 445, respectively, may include filters, shutters, or gates which may operate under the control of the controller 410 and act to pass or block light from passing therethrough based upon one or more control signals transmitted from the controller 410 to the shutter 415 so as to allow only right or left images to be projected upon the FPA 430 at any one time.

Thus, to ensure that only a right image is projected upon the FPA 430, the right shutter opening 440 may be opened so as to allow light to pass therethrough and the left shutter opening 445 may be substantially or fully closed so as to block light from passing therethrough. Accordingly, the FPA 430 may be controlled to capture a right image (e.g., at a given wavelength). Thus, to ensure that only a left image is projected upon the FPA 430, the left shutter opening 445 may be opened so as to allow light to pass therethrough and the right shutter opening 440 may be substantially or fully closed so as to block light from passing therethrough. Accordingly, the FPA 430 may be controlled to capture a left image or a portion thereof (e.g., a red, green, or blue portion/sub-image). Thus, for example, the right pupil may be blocked and light may be allowed to pass only through the left pupil, and vice verse. The shutter may include a liquid crystal (LC) type shutter which may be electronically controlled (e.g., by the controller 410) to allow light to pass or block light from passing through a corresponding right or left pupil 440 and 445, respectively. The controller 410 may apply a voltage to right or left shutter covering the right and left pupils 440 and 445, respectively, to control a state (e.g., open or blocked) of a corresponding shutter. However as described, it is also envisioned that the shutter 415 may include a mechanical shutter portion (e.g., a rotating disk or a linear shutter coupled to a motor controlled by the control portion 410) which may be mechanically rotated or linearly moved back and form between the two pupils 440, 445, to block one of the pupils.

FIG. 4B is a front view of the endoscope system 400 in accordance with an embodiment of the present system. The shutter 415 may be mounted at the distal end of the endoscope 400. The shutter 415 is shown in a position covering or closing the left pupil 445 such that light cannot pass through the left pupil 445. Conversely, the right pupil 440 is shown in an open position in such that light can pass through the right pupil 440. Accordingly images of, for example, the ROI 115 may only pass through the right pupil 440 and will not pass through the left pupil 445 at the present cycle.

In the various embodiments of the present system, instead of illumination with colored light and use of a monochrome FPA, white light may be used along with a color FPA or an FPA having a color filter. For example, in the embodiment shown in FIGS. 4A-4B as well in the other described embodiments, the illumination portion 420, 420' may provide white light and the FPA 430 may include a color FPA which may form color images. A color FPA may include, for example, a monochrome FPA with a color filter array of RGB filters situated at, for example, the right and left shutter openings 440 and 445, respectively. The color filters may include an RGB filter group and may be provided on, for example, a wheel (e.g., a rotating wheel as discussed elsewhere) or may be controlled by the controller 410, or a further controller/processor, so as to block certain colors and/or to allow other colors to pass therethrough. Accordingly, color images may be formed using a monochrome FPA with color filters (e.g., RGB) at the pupils/lenses 440, 445, such as Conjugated Multi-Bandpass Filters (CMBFs) and/or tunable filters that may be tuned by the controller or processor 410 to each one of desired bands selectively, synchronized by the processor with the illumination, such as with 3 or 6 illumination sequences to capture 3 sub-images (where right and left images are simultaneously imaged on right and left sides of the FPA, for each of the red (R), green (G) and blue (B) colors, or any desired colors) or 6 sub-images (where each of the 6 RGB right and left sub-images are imaged on the substantially entire area of the FPA).

In this case, the ROI 115 may be illuminated with colored light (e.g., instead of white light) to sequentially provide RGB images to the FPA through the CMBFs or tunable filters formed over or integrated with the right and left pupils/lenses 440, 445.

Shutters may be used with RGB light under the control of the controller 410 so as to pass certain colors and block other colors at certain times. Accordingly, the controller 410 may include functionality to synchronize the shutters (either mechanical shutters or LC shutters) with the illumination such that, for example, red light is provided (e.g., by the illumination source) when a color (e.g. R, G, or B) filter is activated or a tunable filter is tuned to pass a desired color light and/or sub-red light.

It is further envisioned that instead of using a shutter or switch to ensure that images are passed though one pupil/lens one at a time, i.e., sequentially, and to eliminate the need to synchronize color illumination with blocking/passing of images through one pupil at a time, matched complementary or Conjugated Multi-Bandpass Filters (CMBFs), and/or a tunable filter(s) may be used. In particular, complementary right ($R_R G_R B_R$) and left ($R_L G_L B_L$) multi-band pass filters are used at the right and left pupils, respectively. Further, the illumination is provided through a multi-band pass filter which is matched to the complementary right ($R_R G_R B_R$) and left ($R_L G_L B_L$) multi-band pass filters located at the right and left pupils/lenses.

The right ($R_R G_R B_R$) and left ($R_L G_L B_L$) conjugated or complementary multi-band pass filters at the right and left pupils do not require energy, have no moving parts, and do not require synchronization, since these right ($R_R G_R B_R$) and left ($R_L G_L B_L$) multi-band pass filters are matched to the illuminating light. Thus, when the ROI is illuminated with $Red_{Right}$ ($R_R$) light, this $R_R$ light will reflect back from the object of interest and enter or pass through only the right pupil through the band pass filter $R_R$ at the right pupil, and is blocked from entering or passing through the left pupil by the left ($R_L G_L B_L$) multi-band pass filter located over the left pupil.

FIG. 5 is a schematic view of an endoscope system 500 in accordance with an embodiment of the present system. The endoscope system 500 may include an endoscope 502 including single bore or housing 505 (instead of having two bores 110, 120 of the dual objective endoscope 100 shown in FIG. 1A). The endoscope system 500 may provide a stereoscopic 3-D image of an object or the ROI 115 inside of the body 182. During use, the endoscope 502 may be inserted into the body 182 through an opening or cavity 184 which, for example, may include a natural opening, an incision, etc. The housing 505 may have a distal end 510 and a proximal end 515, where the distal end 510 is insertable into the cavity or opening 184 of the body 182. An imaging device 325 for obtaining optical images of the ROI 115 is located at the distal end 510 and may include an imager or FPA 330 which may capture images projected thereon, a processor to process the images captured by the FPA 330 and to form output signals such as video signals. The processor may include ISOC circuitry 340 or other suitable processor(s), where the ISOC including the processor(s) 340 is behind the FPA 330 and has the same footprint of the FPA 330, where a length or diameter of the footprint may be 4 mm or less, such as 1-4 mm including any sizes therebetween, such as 3-4 mm, 2-4 mm, 2-3 mm, etc.

The imaging device 325 device may be coupled to one or more of an illumination source 550, a display 555, and a controller 595 using wired and/or wireless coupling techniques and/or connecting devices. For example, a cable 545 may couple the imaging device 325 to the illumination source 550, the display 555, and/or the controller 595. The cable 545 may include a signal line to transmit video signals (e.g., from the ISOC) to the display 555 for displaying the optical images of the ROI 115 in multi-dimensions (e.g., 3D, etc.). It is further envisioned that a wireless coupling may be used to transmit the video signals from the ISOC 340 to the display 555. The cable 545 may include one or more light guide to channel light from the illumination source 550 to the illuminators 150 at the front end of the imaging device 325. However, it is also envisioned that the illuminators may be incorporated within the imaging device 325 so as to illuminate the ROI 115 under the control of the controller 595.

The imaging device 325 may include a single focal plane detector array such as the FPA 330 at a front end 565 (of the imaging device 625) facing the region of interest (ROI) 115 for capturing images of the ROI 115. The imaging device 325 may further include processing circuits having suitable processors such as, for example, the ISOC 340 which may be located at a back end 575 (of the imaging device 325) behind the FPA 330 and may have the same footprint as the FPA 330 so that the ISOC 340 does not enlarge an outer cross section 580 of the imaging device 325, where the cross section 580 may be less than 4 mm, such as between 1-4 mm. The ISOC 340 may be operative to convert the optical images captured by the FPA 330 into the video signals for display on the display 555.

A front view of the endoscope 502 in accordance with an embodiment of the present system is shown in FIG. 6. The imaging device 325 may include right and left pupils 585 and 590, respectively, which have complementary right ($R_R G_R B_R$) and left ($R_L G_L B_L$) multi-band pass filters, respectfully, where a single lens 730 (FIG. 7A) in the single bore or housing 505 (unlike the dual lenses 112, 122 in the two bores 110, 120 of FIG. 1A) projects right and left images on the FPA 330. Thus, the right and left pupils 585 and 590 are different from the right and left lenses 112 and 122, respectively, of the dual objective endoscope of FIG. 1A which independently and simultaneously images right and left images on an FPA. An area of a cross section 580 of the endoscope 502 is compact so as to easily pass through an opening or incision in a body.

During operation, the right pupil 585 receives a right image through a right multi-band pass filter (such as Conjugated Multi-Bandpass Filters (CMBFs) 710, 720 shown in FIG. 9) having right three pass bands $R_R G_R B_R$ 710 as illustrated in FIGS. 7 and 9. In a similar manner, the left pupil 590 receives a left image through a left multi-band pass filter (such as filter 720 shown in FIGS. 7 and 9) having left three pass bands $R_L G_L B_L$ as illustrated in FIG. 9 which is a graph illustrating pass bands and stop bands 910, 920 of a Conjugated Multi-Bandpass Filters (CMBFs) 710, 720 in accordance with an embodiment of the present system. As shown in FIG. 9, the right multi-band pass filter 710 having the right three pass bands $R_R G_R B_R$ is the complement of the left multi-band pass filter 720 having left three pass bands $R_L G_L B_L$. That is, the pass bands $R_R G_R B_R$ of the right multi-band pass filter 710 corresponds to the stop bands 920 of the left multi-band pass filter 720. Similarly, the pass bands $R_L G_L B_L$ of the left multi-band pass filter 720 corresponds to the stop bands 910 of the right multi-band pass filter 710.

FIG. 7A is a schematic view of the imaging device 325 components of the endoscopic system 500 (FIG. 5) in accordance with an embodiment of the present system. The imaging device 325 may further include a lens system 730. The lens system 730 may include several lenses, such as an objective lens and a focusing lens for imaging the right image 740 and the left image 750 directly on the (single) FPA 330. The illuminators 150 (see also FIGS. 4D and 6) illuminate the ROI 115 through Conjugated Multi-Bandpass Filters (CMBFs) 810 (shown in FIG. 8), having the right three pass bands ($R_R G_R B_R$) and the left three pass bands ($R_L G_L B_L$). The multi-band pass filter 810 may be matched to the right multi-band pass filter 710 and the left multi-band pass filter 720 (FIGS. 7A-7B and 9) covering the right and left pupils, respectively, so that when the ROI 115 is illuminated with one color light, such as in the right red band $R_R$, then this $R_R$ light reflected from the ROI 115 passes through the right pupil 585 through the pass band $R_R$ of the right multi band filter 710 $R_R G_R B_R$ covering the right pupil 585, and is blocked from passing through the left pupil 590 by the stop band 920 (FIG. 9) of the left multi band filter 720 $R_L G_L B_L$, covering the left pupil 590. After six sequential illuminations by any sequence of lights in the bands $R_R G_R B_R$ $R_L G_L B_L$, where each of the six sub-images is imaged on the entire FPA (as will be described in connection with FIG. 11A) a full color image is achieved. As previously described and will be described in connection with FIG. 11B, both right and left images, e.g., $R_R$ and $R_L$ images, may be simultaneously imaged on the FPA, by simultaneously illuminating the ROI with both a right color and a left color (e.g., $R_R$ and $R_L$ simultaneous illumination), then a full color image is obtained after three sequential illuminations. Although, the illumination source 550 (see also FIG. 5) may be situated remotely from the endoscope 502, it is also envisioned that the illumination source 550 may be situated within the housing 505 of the endoscope 502 and may be adjacent to or formed integrally with the illuminators 150.

As shown in FIG. 7B the right and left conjugated multi-bandpass filters (CMBFs) 710', 720', used to pass right and left sub-images $R_R G_R B_R$ $R_L G_L B$, may each have a semicircular shape which are placed next to each other to form a full circular conjugated multi-bandpass filter which may be placed over a lens and/or a transparent support substrate, such as removably placed on a front and/or a back surface of the lens and/or the transparent support substrate, or removably inserted into an objective lens, or integrated with a lens, to form and/or cover the right and left pupils of the imaging device 325. This provides for easily converting the binocular two-pupil imaging unit or camera 325 into a monocular camera by simply removing the CMBF pair 710', 720' allowing a user/operator of the endoscope to select between binocular and monocular imaging to obtain better images depending on the environment and desired viewing distances. For example, monocular imaging may be selected and used to view long viewing distances, where depth perception is not as important, while binocular imaging to obtain depth perception may be used for viewing short distances.

Illustratively, for a working distance of 6 to 12 mm, the binocular imaging systems using the CMBF pair 710, 720 (710', 720') provides better depth resolutions than that without the CMBF over the viewing distances range between 6 to 12 mm. Improved depth perception or depth resolution is provided at working or viewing distances of 5 mm to 2 cm with a 60 degree field of view using a negative or wide angle lens by the embodiments using right and left lenses or openings/apertures separated by a distance between 0.5 mm to 2 mm, such as a distance of 1 mm, as well as the embodiments where the right and left images are captured by the semicircular CMBF pair 710', 720' shown in FIG. 7B.

FIG. 8 is a schematic view of an illumination source 550 (also shown in FIG. 5) of the endoscope 500 in accordance with an embodiment of the present system. The illumination source 550 may include a plurality of sources 830, 832, 834, 840, 842, 844 and corresponding pass band filters (PBFs) $R_R$, $G_R$, $B_R$, $R_L$, $G_L$, and $B_L$ of a multi bandpass filter 810. The sources 830, 832, 834, 840, 842, and 844 may include any suitable white light sources such as Xenon sources, etc.

The controller 595 (also shown in FIG. 5) may control the illumination source 550 such that the illumination source 550 sequentially turns on the light sources 830, 832, 834, 840, 842, 844 one at a time so as to illuminate the ROI 110 via light guide(s) 820 and the illuminators 150 of the imaging device 325. If desired, lenses 825 may also be provided between the CMBFs 810 and the light guide(s) 820. Accordingly, light from the sources 830, 832, 834, 840, 842, 844 may pass through the corresponding illumination pass-band filters (PBFs) $R_R$, $G_R$, $B_R$, $R_L$, $G_L$, and $B_L$ of the illumination multi bandpass filter 810 so that the region of interest (ROI) 115 is illuminated one at a time by light within one of the three right pass bands ($R_R G_R B_R$) and the three left pass bands ($R_L G_L B_L$) during each illumination interval. During each illumination interval, the illuminating light is reflected from the ROI 115 and is passes through the right or left multi-band pass filter 710, 720 (shown in FIGS. 7A-7B) covering the right and left pupils 585, 590 to form an image of the ROI 115 projected upon substantially the whole or entire area 1110 (FIG. 11A) of the single FPA 330 and processed by an image processor such as the ISOC 340. Then, after six illumination intervals, namely by lights in the bands of $R_R G_R B_R$ and $R_L G_L B_L$, the individual images may captured by the FPA 330 may be superimposed to form a full color image. For example, the image data from the ISOC 340 is processed using an algorithm at the display site to combine and form 3D images from the 3 or 6 sub-images and/or image data. The right and left images may be superimposed at the viewing plane of the display 555. Thus, after six illumination intervals, three (RGB) right images are superimposed over each other on the entire FPA area 1110 (FIG. 11A) and three (RGB) left images are superimposed over each other also on the entire FPA area 1110. Six image information or data are processed and correlated by a processor to form 3D images displayed on a display 555 (FIG. 5). In summary, six images may be used to form the full color formed on substantially the entire FPA area 1110 (FIG. 11A). That is, each one of the six images $R_R$, $G_R$, $B_R$, $R_L$, $B_L$ (in any sequence) may be formed on the entire area 1110 (FIG. 11A) of the FPA 330.

Any sequence of illumination using the six Xenon (white) light sources may be used, where three ($R_R G_R B_R$) right sub-images may be collected and superimposed to form a right image, and three ($R_L G_L B_L$) left sub-images may be collected and superimposed to form a left image. That is, the illumination to provide the six sources 830, 832, 834, 840, 842, 844 may be in any sequences such as $R_R$, $G_R$, $B_R$, $R_L$, $G_L$, $B_L$, or $R_R$, $R_L$, $G_R$, $G_L$, $B_R$, $B_L$, etc. It should be noted that since each color is divided into right and left bands, such as $Red_{Right}$, ($R_R$) and $Red_{Left}$ ($R_L$), the right and left images are not exactly the same color, but are metamers.

Further, instead of collecting the full color image after six illuminations (where each of the six images is formed on the entire FPA 330), a full color image may be collected after three illuminations (where each right and left image is simultaneously projected on respective right and left halves 1150, 1155 of an image capture portion such as the FPA 330' of FIG. 11B) using only three Xenon (white) light sources, with three multi-band pass filters, namely, a first Xe light source that provides light through a filter having the bandpass of $R_R$, $R_L$, a second Xe light source that provides light through a filter having the bandpass of $G_R$, $G_L$, and a third Xe light source that provides light through a filter having the bandpass of $B_R$, $B_L$. Thus, after the first illumination using light in the band $R_R$, $R_L$, right and left red images are simultaneously imaged on right and left FPA areas (e.g., see, 132, 134 of FIGS. 1B and 1155 and 1150 of FIG. 11B) the second illumination with light in the band $G_R$, $G_L$ is used to image right and left green images simultaneously on the right and left FPA areas 132, 134 (where the green images are superimposed on the red images), and the third illumination with light in the band $B_R$, $B_L$ is used to image right and left blue images simultaneously on the right and left FPA areas 132, 134 (where the blue images are superimposed on the previously images red and green images). Again, any sequence of illumination using three Xenon (white) light sources may be used, such as $R_R R_L$, $G_R G_L$, $B_R B_L$ or $G_R G_L$, $R_R R_L$, $B_R B_L$, etc.

FIG. 10A is a schematic view of a system 1000A in accordance with an embodiment of the present system. The system 1000A may be similar to the endoscope system 500. However, the system 1000A may include two white light sources (e.g., Xenon, etc.), as will be discussed below, which provide illumination instead of three white (Xenon) light sources for illumination to form the right image and another three Xe light sources for illumination to form the left image as was described above in connection with the embodiment of FIG. 8. Accordingly, the system 1000A includes one right light source 1010 is for illumination to form the right image, and one left light source 1020 is for illumination to form the left image. This is achieved using a right rotating wheel 1080 having a single opening 1085 for sequentially illuminating RGB right channels or light guides 1070, 1072, 1074 (inside the endoscope 502) that include RGB filters, respectively, such as at their entrance or exit ends 1050, 1060, similar to the embodiment described in connection with FIG. 2C. Similarly, a left light source 1020 provides white light through the opening 1087 of a left rotating wheel 1082 for sequentially illuminating one at a time the entrance side 1050 of left channels or light guides 1075, 1077, 1079 that include RGB filters, respectively. The right and left light sources 1080 and 1020, respectively, may be controlled by the controller 595 (FIG. 5). Similarly, the right and left wheels 1085 and 1082, respectively, may be controlled by the controller 595 (FIG. 5) to rotate at a desired angular frequency (ω) and may be synchronized with operation of the right and left sources 1080 and 1020, respectively, and/or the FPA. The right and left light guides 1070, 1072, 1074, 1075, 1077, 1079 are coupled to the illuminators 150 for illuminating the ROI 115.

FIG. 10B is a schematic view of a system 1000B in accordance with an embodiment of the present system. In the system 1000B, light from a white source 1010 such as a Xenon lamp may be selectively passed through single rotating wheel 1083 having first, second and third apertures 1038R, 1038G, and 1038B, respectively, used to receive white light from the source 1310, for example. The three apertures 1038R, 1038G, and 1038B are respectively covered with, or include, red, green, and blue filters, where each filter includes both the right and left band portions. More particularly, the first aperture 10388 is includes a $R_R R_L$ filter, the second aperture 1038G includes a $G_R G_L$ filter and the third aperture 1038B includes a filter $B_R B_L$ filter. Accordingly, the three apertures 1038R, 1038G, and 1038B each may pass light of a different color spectrum as illustrated in FIG. 10C which is a graph of colors passed through the first through third apertures 1038R, 1038G, and 1038B, respectively, in accordance with an embodiment of the present system. During use, $R_R R_L$, $G_R G_L$, and $B_R B_L$ filters of the first, second and third apertures 1038R, 1038G, 1038B, respectively, may pass corresponding colors and block other colors of light from the source 1310 as the wheel 1383 rotates. Thus, rotation of the wheel 1083 with the thee apertures simultaneously provides both right and left one color (e.g., red, green, and blue, in sequence) illumination for simultaneously imaging both right and left red images on the right and left areas 1150, 1155 of the FPA 330' shown in FIG. 11B. Accordingly, after three illuminations with $R_R R_L$, $G_R G_L$, $B_R B_L$ in any sequence, the image information obtained from the FPA 330' may be processed and a corresponding full color image is obtained.

FIG. 11A shows an imaging system 1100A having an endoscope with a single lens 1130 in accordance with an embodiment of the present system. In response to sequential illumination, where light having the half-band of a color sequentially (or one at a time) illuminates the ROI 115 (namely, by six sequential illumination in any order using the following six colored lights $R_R$, $R_L$, $G_R$, $G_L$, $B_R$, $B_L$), the single lens 1130 may sequentially receive one at a time six sub-images of the right and left images from the right and left multi-band pass filters 710 and 720, respectively, covering the right and left pupils 585 and 590, respectively. The single lens 1130 may form the image on the entire (or a substantial portion of) an image capture area 1110 of the FPA 330. The system may process six sequential images captured during six sequential illuminations and process the six sequential images to form a full stereo (e.g., right and left) color image. The six sequential images may correspond with a sequential formation of RGB right and RGB left images on the entire image capture area 1110 of the FPA 330 (in any sequence such as $R_R$, $G_R$, $B_R$, $R_L$, $G_L$, $B_L$, or $R_R$, $R_L$, $G_R$, $G_L$, $B_R$, $B_L$, etc.). Thus, the entire or a substantial portion of the image capture area 1110 of the FPA 330 may be used to from a single image. With regard to the FPA 330, it may have a cross section (e.g., an image capture area) which is shaped and sized such that an image of sufficient detail may be captured. For example, as shown, the FPA 630 may include a circular cross section 1120. Of course, that shape of the FPA cross section and/or FPA image portions may any shape, such as circular, oval, square, rectangular, etc.

FIG. 11B shows an imaging system 1100B having an endoscope with a dual lens configuration in accordance with an embodiment of the present system. The endoscope system 1100B is similar to the endoscope system 1100A. However, the endoscope system 1100B includes two lenses 1140, 1145 (as opposed to a single lens). In response to simultaneous illumination with both right and left sub-colors, the two lenses 1140, 1145 may simultaneously receive right and left images from the right and left multi-band pass filters 710 and 720, respectively, covering the right and left pupils 885 and 890, respectively. Each of the two lenses 1140 and 1145 projects an image of a ROI 115 on a half the FPA area. In particular, the right lens 1140 forms an image on the right FPA area 1150 (e.g., a right halve) and the left lens 1145 forms an image on the left FPA area 1155

(e.g., left halve). To minimize cross sectional area, the FPA may have an oval cross section 1160. However, other shapes and sizes are also envisioned. Of course, instead of the two lenses 1140, 1145, a single lens (such as the lens 1130 shown in FIG. 11A) may be also be used to simultaneously receive right and left images from the right and left multi-band pass filters 710 and 720, respectively, in response to simultaneous illumination with both right and left sub-colors, such as a first illumination using red right and left lights $R_R$ and $R_L$, followed by a second illumination using $G_R$ and $G_L$, and again followed by a third illumination using $B_R$ and $B_L$, for example. Accordingly, a full color stereo (right and left) color image is formed using image information which corresponds with images from three sequential illuminations, each of which may correspond with:

$R_R$, $R_L$ red right and left images formed (at one sequence) simultaneously on the right and left halves 1150 and 1155, respectively, of the FPA 330', such as at the first sequential illumination;

$G_R$, $G_L$ green right and left images formed at another sequence, such as at the second sequential illumination to simultaneously form right and left green images on the right and left halves 1150 and 1155, respectively, of the FPA 330', and $B_R$, $B_L$ blue right and left images formed at the final sequence to simultaneously form right and left green images on the right and left halves 1150 and 1155 of the FPA 330'.

After three time-sequential illuminations, three (superimposed) right and left images formed on the right and left halves 1150, 1155 of the FPA 330'. The three time-sequential illuminations provide three illuminations in the following three bands $R_R R_L$, $G_R G_L$, $B_R B_L$ in any sequence ($G_R G_L$, $R_R R_L$, $B_R B_L$, or $B_R B_L$, $G_R G_L$, $R_R R_L$ etc.) Of course, if desired, the full color image may be formed after six sequential illuminations for providing light in the six bands sequentially, $R_R$, $G_R$, $B_R$, $R_L$, $G_L B_L$, or in any other sequence.

It is also envisioned that a triangulator may be provided to adjust an alignment of imaging portions (e.g., lenses, etc.) apparatus such that they may be parallel or non-parallel (e.g., toed inward) to each other. The triangulator may be controlled by automatically by a controller/processor and/or manually by a user.

The imaging systems discussed above may be incorporated into endoscopes such as scissor-type rotating angle MIS endoscopes as will be discussed below with reference with FIGS. 12A through 21.

FIG. 12A shows a front perspective view of a stereoscopic imaging system 1200 in accordance with an embodiment of the present system. The stereoscopic imaging system 1200 may include an imaging portion which has two lenses 1214 so as to capture stereoscopic images as described above. Illuminators 1212 may receive light (e.g., RGB, or white light) from a light source (e.g., LEDs, Xenon bulbs, etc.) via a light guide(s) such as a fiber optic cable(s) 1204, and emit light for illuminating a ROI for viewing and/or image capture. However, it is also envisioned that the illuminators 1212 may include light from, for example, one or more light sources situated within the body portion 1202 which may include a lens barrel 1210 attached thereto. The body portion 1202 may be sized and/or shaped as desired (e.g., round, square, oval, etc.). An image capture portion, such as a CCD (Charge-Coupled Device), CMOS (Complementary Metal Oxide Semiconductor device), FPA, etc., and/or an image processing portion may be included within the body portion 1202. The FPA may capture images projected thereon by one or more lenses, filters, pupils, etc., situated within the lens barrel 1210. The processing portion may process the images for transmission via, for example, one or more power and signal cables 1206 to be displayed on a display. The lens barrel 1210 may be attached to the body portion 1202 via an interface 1208 such as a bayonet mount, etc. Accordingly, the lens barrel may be swapped and/or removable from the body portion 1202.

FIG. 12B shows a rear perspective view of a stereoscopic imaging system 1200 of FIG. 12A in accordance with an embodiment of the present system. The imaging portions of the present system may be incorporated with endoscopes, robotic arms, etc. such as is shown elsewhere in the description. However, it is also envisioned that the stereoscopic imaging system 1200 may include wireless communication portions which may wirelessly receive and/or transmit information.

FIG. 13 illustrates a stereoscopic imaging device 1300 in accordance with an embodiment of the present system. The stereoscopic imaging device 1300 may provide forward and rearward views of a ROI and may be similar MIS tools as described in U.S. Patent Application No. 2009/0187072 the contents of which are incorporated herein by reference. The stereoscopic imaging device 1300 may include body portion 1318, handles 1306, a shaft 1310, a linkage portion 1312, a stereoscopic imaging portion 1302, and a mirror, a lens portion and/or imaging systems 1304 (such as including a camera portion 1402, 1802 shown in FIGS. 14-18B). The linkage portion 1312 may be coupled to one of the scissor-type handles 1306 such that movement of the coupled scissor-type handle 1306 may result in displacement of the linkage portion 1312. The stereoscopic imaging portion 1302 may be coupled to the linkage portion 1312 such that displacement of the linkage portion 1312 may cause the stereoscopic imaging portion to be rotationally displaced or otherwise deflected so as to change a viewing direction. The stereoscopic imaging portion 1302 may capture images which are reflected off of a reflective portion such as mirror 1304 so as to capture images of an ROI 115 in a rearward viewing direction (in relation to the a longitudinal axis of the shaft 1310) illustrated by arrow 1308 at one or more viewing angles. The angle of the mirror or imaging system 1304 may be adjusted and locked in position so that a desired viewing angle may be obtained. Further, the mirror or other imaging systems may be removed (or otherwise adjusted) so that the stereoscopic imaging portion 1302 may capture a forward view as illustrated by arrow 1309. As will be described, instead of or in addition to the mirror 1304, the imaging portion 1302 may include rotary devices to rotate the imaging portion 1302, or parts thereof, in order to provide rearward viewing.

FIG. 14 illustrates an endoscope 1400 in accordance with an embodiment of the present system. The endoscope 1400 may be similar to the endoscope 1300 (FIG. 13) and may include one or more of a body portion 1418, handles 1406, a shaft 1410, a distal end portion 1422, cables 1412 including a light guide(s) shown as reference numeral 1420 in FIG. 16, and a camera portion 1402. The body portion 1418 may be coupled to the handles 1706 such that one handle 1406 of the handles 1406 may move relative to the body portion 1418. The shaft 1410 may be coupled at a proximal end to the body portion 1418 and may be coupled to the distal end portion 1422 at its distal end. The shaft 1410 may include an opening for receiving a rod (e.g., see, 1416, FIGS. 15-17) which may be coupled at a proximal end to one of the handles 1406 and may be coupled at a distal end to a gear rack 1432 (FIG. 17) such that displacement of one handle 1406 relative to the other handle 1406 may cause displacement of rod 1416 and the gear rack 1432 in a direction which may be parallel to the longitudinal axis 1413 of the shaft. The camera portion 1402 may be rotatably coupled to the distal end portion 1422 at pivot 1423 (FIG. 18) such that the camera portion 1402 may rotate about a pivot axis 1414 as illustrated by arrow 1417 (FIG. 14). The rotation may be greater than 120 degrees as indicated by arrow 1419 (FIG. 14). Accordingly, the camera portion 1402 may rotate by about ±120 degrees horizontally about its pivot axis 1414.

As shown in FIGS. 14-15 and 17, the camera portion 1402 may include a pinion 1430 (FIG. 17) which may engage the gear rack 1432 such that movement of the rod 1416 (e.g., caused by displacement of the handle portion 1406 coupled thereto) in a direction which is longitudinal to the shaft 1410 may cause the camera to rotate about the pivot axis 1414. Accordingly, when the handle 1406 which is coupled to the shall is displaced relative to the other handle 1406, the rod 1416 is displaced in a direction which is relative to the longitudinal direction of the shaft 1410. The cables 1412 may include a light guide and/or transmission reception cables, etc. for transmitting (e.g., image information, etc.) and receiving (e.g., control commands, power, etc.) various information and/or power. However, it is also envisioned that information may be transmitted and/or received using a wireless communication method. The light guide 1420 may include a fiber optic line which may couple an illuminator (e.g., see, 1442, FIG. 16) of the camera portion 1402 to a light source such as a Xenon, LED, or other light source.

FIG. 14 is a detailed view of the distal end portion 1422 of the endoscope 1400 (shown by a dotted circle labeled 15 in FIG. 14) in accordance with an embodiment of the present system. The camera portion 1402 is shown rotatably displaced such that side facing images may be captured. The rod 1416 may be held in position against the pinion (e.g., see, 1430, FIG. 17) by a rail or track 1432.

FIG. 16 is a detailed view of the distal end portion 1422 of the endoscope 1400 (FIG. 14) in accordance with an embodiment of the present system. The camera portion 1402 may include a body portion 1436 which may include two lugs 1438 which may engage corresponding openings 1440 in the distal end portion 1422 which may define the pivot axis 1414 (FIGS. 17-18) about which the camera portion 1402 may rotate.

In another embodiment, a rotatable interface between the light guide 1420 and the camera 1402 provides for easier rotation of the camera 1402. The rotatable interface comprises the at least one periscope which may be used along with at least one fiber optic cable to direct light from light sources to the distal end of the camera to illuminate the ROI 115. Illustratively, one of the lugs 1438 comprises the periscope connected to the light guide 1420, e.g., a fiber optic cable that receives light from a light source(s) and provides light to one end of the periscope. The periscope comprises angled reflectors e.g., at 45 degrees, for directing light from one (or entrance) end to another (or exit) end of the periscope. The angled reflectors may be one mirror at the periscope entrance end to receive light from the fiber optic 1420 and reflect light to another mirror located at the exit end of the periscope. The second mirror reflects the light from the first mirror to exit out of the periscope exit end and to reflect from a surface, such as the internal surface of the camera portion 1402, which is internally coated. Light reflected from the internal surface of the camera housing is directed to exit from the front surface of the camera to illuminate the ROI 115. For example, the reflected light exits from the periphery of the camera front surface shown as an illuminator 1442 in FIG. 16.

The body portion 1436 may include the illuminator 1442, which may comprise a diffuser to provide diffused illumination of the ROI, for example, from around the body periphery. The illuminator 1442 may include an optically conductive material (e.g., glass, plastic (e.g., polycarbonate), mineral, etc.) and which may have an optically reflective coating 1446 (FIG. 17) applied to a surface thereof, such the internal surface that receives light from the periscope exit end and reflect the light out to form the illuminator 1442. Accordingly, light which enters the optically conductive material of the body portion 1736 (e.g., from the light source via the light guide 1420) may be directed outward from a front side of the illuminator 1442 as illustrated by arrow 1448. The illuminator 1442 may be coupled to the light guide 1420 using any suitable method such as a mirror, an optical slip ring, direct coupling, etc. An image capture portion 1454 may capture images which may be processed and/or transmitted on a display of the system. The image capture portion 1454 may include a stereoscopic imaging apparatus as disclosed herein, e.g., an FPA, or may include a commercial off the shelf (COTS) camera(s) such as a wireless PILLCAM™ or the like.

FIG. 17 is a detailed view of the camera portion 1402 of the endoscope 1400 in accordance with an embodiment of the present system. The pinion 1430 may be attached to or formed integrally with a corresponding one of the lugs 1418 and is shown engaging the gear rack 1432. The image capture portion 1454 may include one or more apertures 1450 through which 2D and/or stereoscopic and/or 3D images may be captured. Accordingly, for example, two inner apertures may be located in an interior portion of the image capture portion 1454 and may view a ROI via the aperture 1450. However, it is also envisioned that two apertures 1450 spaced apart from each other may also be included, as described.

FIG. 18A is a detailed view of a distal end portion 1822 of an endoscope 1800 in accordance with an embodiment of the present system. The endoscope 1800 may be similar to the endoscope 1400 of FIG. 14. However, the camera portion 1802 may include apertures 1850 (through which images may be captured) to provide a forward view shown by arrow 1860 in FIG. 18B. The camera portion 1802 is handedly or rotatebly attached via the two lugs 1438 which in this case are offset from a centerline of the camera portion 1802 such that the camera portion 1802 may be rotated by about 180 degrees about its offset pivot axis 1814' to provide a rearward view, shown by arrow 1865 in FIG. 18B, which is substantially along a longitudinal axis of a shaft portion 1810 (which is similar to shaft 1410 shown in FIG. 14) to which a distal end portion 1822 is attached. An illuminator 1842 may be similar to the illuminator 1442 (shown in FIGS. 14-17) and may provide illumination to an ROI.

FIG. 19 shows a flow diagram that illustrates a process 1900 in accordance with an embodiment of the present system. The process 1900 may be performed using one or more computers and/or processors, e.g., communicating over a network. The process 1900 can include one of more of the following acts. Further, one or more of these acts may be combined and/or separated into sub-acts, if desired. In operation, the process may start during act 1901 and then proceed to act 1903.

During act 1903, the process may capture images in accordance with an embodiment of the present system. Accordingly, the process may perform a stereoscopic image capture process to capture a plurality of left and/or right images of an ROI 115, as described, using illumination from one or more sources. Then, the process may continue to act 1905.

During act 1905, the process may digitize and process the right and left images captured during act 1903 so as to form corresponding stereoscopic image information, e.g., using ISOC (340 in FIG. 3) and/or processor(s)/controller(s) 2010 shown in FIG. 20. Then, the process may continue to act 1907.

During act 1907, the process may display the processed stereoscopic images information, e.g., on a rendering device 2030 (FIG. 20) such as the display 555 shown in FIG. 5, using a method suitable for displaying stereoscopic images. Then, the process may continue to act 1909.

During act 1909, the process may store the processed stereoscopic image information in a memory 2020 (FIG. 20 of the system. Then, the process may end at act 1911.

FIG. 20 shows a portion of a system 2000 (e.g., stand alone system, peer, server, device interconnected through a network, wired and/or wireless, etc.) in accordance with an embodiment of the present system including an endoscopic unit 2090 connected to a network 2080 and a user interface input/output device 2070. For example, a portion of the present system may include a processor 2010 operationally coupled to a memory 2020, a display 2030, a camera portion 2040, and a user input device 2070. The memory 2020 may be any type of device for storing application data as well as other data related to the described operation. Application data, e.g., stored in memory 2020, and other data are received by the processor 2010 for configuring (e.g., programming) the processor 2010 to perform operation acts in accordance with the present system. The processor 2010 so configured becomes a special purpose machine particularly suited for performing in accordance with the present system, such as to correlate right and left sub-image information to form a stereoscopic 3D image information for display on the rendering device, e.g., display 2030.

The camera portion 2040 may include one or more lenses 2042, filters 2044, image capture portion 2046 (e.g., an FPA, etc.), and an illuminators 2048 and may operate under the control of the processor 2010. The camera portion 2040 may operate as a still camera, a video camera, a 3D camera, etc. The processor may control or be configured to control process the image information from the camera portion, may form corresponding image information (such as 3D image information), and may store the processed image information in accordance with one or more standards such as, for example, an MPEG4 (Motion Picture Experts Group-4) standard. The processor may control or also be further configured to control light sources (e.g., LEDs, Xenon bulbs, etc) which may provide light such as white light or RGB (e.g., red, green, and/or blue) light to the illuminators 2048. The system may further include a synchronizer, and/or the processor may be further configured to synchronize operation (e.g. timing, etc.) of one or more of the light sources, illuminator, optical filters, optical image capturing devices (e.g., the FPA), and image processors to operate in synch with each other. Further, the system may include an image correlator, and/or the processor may be further configured to correlate data and/or sub-images captured by the image capturing devices (e.g., the FPA) and form therefrom full 3D and/or stereoscopic images, such as by superimposing 3 or 6 sub-images obtained during illumination sequences, for example, obtained during 3 or 6 sequences of illumination with different color lights, as described.

The operation acts may include requesting, providing, and/or rendering of content such as processed image information to render images such as stereoscopic/3D images on a display of the system. The user input 2070 may include a keyboard, mouse, trackball, scissor mechanism, lever, remote control, or other device, including touch sensitive displays, which may be stand alone or be a part of a system, such as part of a personal computer, personal digital assistant, mobile phone, set top box, television or other device for communicating with the processor 2010 via any operable link. The user input device 2070 may be operable for interacting with the processor 2010 including enabling interaction within a UI as described herein. Clearly the processor 2010, the memory 2020, display 2030 and/or user input device 2070 may all or partly be a portion of a computer system or other device such as a client and/or server as described herein.

The methods of the present system are particularly suited to be carried out by a computer software program, such program containing modules corresponding to one or more of the individual steps or acts described and/or envisioned by the present system. Such program may of course be embodied in a computer-readable medium, such as an integrated chip, a peripheral device or memory, such as the memory 2320 or other memory coupled to the processor 2310.

The program and/or program portions contained in the memory 2020 configure the processor 2010 to implement the methods, operational acts, and functions disclosed herein. The memories may be distributed, for example between the clients and/or servers, or local, and the processor 2010, where additional processors may be provided, may also be distributed or may be singular. The memories may include a non-transitory memory. The memories may be implemented as electrical, magnetic or optical memory, or any combination of these or other types of storage devices. Moreover, the term "memory" should be construed broadly enough to encompass any information able to be read from or written to an address in an addressable space accessible by the processor 2010. With this definition, information accessible through a network is still within the memory, for instance, because the processor 2010 may retrieve the information from the network for operation in accordance with the present system.

The processor 2010 is operable for providing control signals and/or performing operations in response to input signals from the user input device 2070 as well as in response to other devices of a network and executing instructions stored in the memory 2020. The processor 2010 may be an application-specific or general-use integrated circuit(s). Further, the processor 2010 may be a dedicated processor for performing in accordance with the present system or may be a general-purpose processor wherein only one of many functions operates for performing in accordance with the present system. The processor 2010 may operate utilizing a program portion, multiple program segments, or may be a hardware device utilizing a dedicated or multi-purpose integrated circuit.

Further variations of the present system would readily occur to a person of ordinary skill in the art and are encompassed by the following claims, including combination various elements of different embodiments, such as using a monochrome or a color FPA with any one of the embodiments, and combinations thereof, using 3, 6 or different numbers of colors/sub-colors for sequential illumination of the ROI and/or formation of images on the single FPA, using the entire FPA to image one sub-image and/or using FPA portions to simultaneously image at least 2 sub-images on at least two portions of the FPA. Through operation of the present system, a virtual environment solicitation is provided to a user to enable simple immersion into a virtual environment and its objects.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. In addition, any section headings included herein are intended to facilitate a review but are not intended to limit the scope of the present system. Accordingly, the specification and drawings are to be regarded in an illustrative manner and are not intended to limit the scope of the appended claims.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function;

e) any of the disclosed elements may be comprised of hardware portions (e.g., including discrete and integrated electronic circuitry), software portions (e.g., computer programming), and any combination thereof;

f) hardware portions may be comprised of one or both of analog and digital portions;

g) any of the disclosed devices or portions thereof may be combined together or separated into further portions unless specifically stated otherwise:

h) no specific sequence of acts or steps is intended to be required unless specifically indicated; and i) the term "plurality of" an element includes two or more of the claimed element, and does not imply any particular range of number of elements; that is, a plurality of elements may be as few as two elements, and may include an immeasurable number of elements.

What is claimed is:

1. An endoscope that provides a stereoscopic three dimensional image of a region of interest inside of a body, the endoscope comprising:
   a housing having a distal end and a proximal end, the distal end being insertable into a cavity of the body;
   an image capture device at the distal end that obtains optical images of the region of interest, and processes the optical images to form video signals;
   a folded substrate folded into a U-shape having first and second legs; and
   a connecting device between the image capture device and the proximal end that connects the image capture device to an illumination source and a display, the connecting device providing the video signals to the display to display the optical images of the region of interest;
   the image capture device comprising:
      a single focal plane detector array at a front end facing the region of interest that obtains the optical images, and processing circuits at a back end behind the single focal plane detector array, the processing circuits processing signals from the single focal plane detector array;
      a right pupil that receives a right image through a right multi-band pass filter having right three pass bands;
      a left pupil that receives a left image through a left multi-band pass filter having left three pass bands, the right multi-band pass filter having the right three pass bands being a complement of the left multi-band pass filter having left three pass bands;
      a single lens that directly receives the right image from the right multi-band pass filter and the left image from the left multi-band pass filter that images the right image and the left image directly on the single focal plane detector array, the single lens having a single continuous portion that entirely covers both the right pupil and the left pupil and directly receives the right image from the right pupil and the left image from the left pupil and directs the right image from the right pupil and the left image from the left pupil to the single focal plane detector array; and
      an illuminator that illuminates the region of interest through a stationary multi-band pass filter having the right three pass bands and the left three pass bands, the stationary multi-band pass filter of the illuminator being identical to the right multi-band pass filter of the right pupil and the left multi-band pass filter of the left pupil so that the stationary multi-band pass filter of the illuminator has filter characteristics that are identical to filter characteristics of the right multi-band pass filter of the right pupil and the left multi-band pass filter of the left pupil, and when the right pupil passes light reflected from the region of interest then the left pupil being blocked from passing the light, and
   the stationary multi-band pass filter dividing a visible spectrum into six contiguous and non-overlapping regions including the right three pass bands being alternately contiguous with the left three pass bands,
   the right three pass bands being separated by right three stop bands that are identical to the left three pass bands, and the left three pass bands being separated by left three stop bands that are identical to the right three pass bands,
   all edges of the right three stop bands coinciding with all edges of the left three pass bands, and all edges of the left three stop bands coinciding with all edges of the right three pass bands,
   the right multi-band pass filter being joined with and contacting the left multi-band pass filter to fit over and entirely cover the single lens, and
   the folded substrate consisting of the single focal plane detector array at an outer side of the first leg facing the single lens and the processing circuits at an outer side of the second leg facing the connecting device that processes the signals from the single focal plane detector array located at the outer side of the first leg.

2. The endoscope of claim 1, wherein the illuminator provides illumination controlled by a controller that illuminates the image capture device through the stationary multi-band pass filter of the illumination so that the region of interest is illuminated one at a time by six respective light beams having identical spectrums as respective spectrums of the six contiguous and non-overlapping regions including the right three pass bands of the right pupil and the left three pass bands of the left pupil.

3. The endoscope of claim 1, wherein the right three pass bands and the left three pass bands are within a visible spectrum having three primary colors so that each primary color is divided into a right primary color and a left primary color, the right primary color being a metamer of the left primary color.

4. The endoscope of claim 1, wherein the connecting device comprises a cable including:
right light guides that provides a right illumination at the illuminator including providing one at a time right sub-lights at the right three pass bands from the right multi-band pass filter; and
a left light guide that provides a left illumination at the illuminator including providing one at a time left sub-lights at the left three pass bands from the left multi-band pass filter.

5. The endoscope of claim 1, wherein the connecting device comprises light guides illuminated by three right white light sources that provides a right illumination including providing one at a time right sub-lights at the right three pass bands from the right multi-band pass filter; the light guides being further illuminated by three left white light sources that provides a left illumination including providing one at a time left sub-lights at the left three pass bands from the left multi-band pass filter.

6. The endoscope of claim 5, wherein the three right white light sources each have a bandpass filter having one of the right three pass bands, and the three left white light sources each have a bandpass filter having one of the left three pass bands.

7. The endoscope of claim 1, wherein the single lens images the right image and the left image, one at a time, on an entire area of the single focal plane detector array.

8. The endoscope of claim 7, wherein a cross section of the image capture device is one of circular and oval.

9. The endoscope of claim 7, further comprising a controller that time-multiplexes the right image and the left image imaged sequentially on the single focal plane detector array.

10. An endoscope system that obtains three dimension (3D) images, the endoscope system comprising:
a stationary illumination multi-bandpass filter which sequentially passes a different color spectrum of light of a plurality of color spectrums of light during an image illumination interval such that a different color of light is passed during each image illumination interval of a plurality of image illumination intervals which form an image illumination period;
an image capture portion which sequentially captures a plurality of images each corresponding with a different color spectrum of light which passes through the stationary illumination multi-bandpass filter during a corresponding image illumination interval of the plurality of image illumination intervals;
an image processing portion which processes the sequentially captured plurality of images for each image illumination interval and forms corresponding 3D image information corresponding with a plurality of the sequentially captured plurality of images;
a folded substrate folded into a U-shape having first and second legs; and
a display which renders the 3D image information,
the image capture portion including a right multi-band pass filter and a left multi-band pass filter, a detector and a single lens having a single continuous portion that entirely covers both the right multi-band pass filter and the left multi-band pass filter and directly receives the right image from the right multi-band pass filter and the left image from the left multi-band pass filter, the single lens directly providing the right image from the right multi-band pass filter and the left image from the left multi-band pass filter to the detector,
the stationary illumination multi-band pass filter being identical to the right multi-band pass filter and the left multi-band pass filter of the image capture portion so that the stationary illumination multi-band pass filter has filter characteristics that are identical to filter characteristics of the right multi-band pass filter and the left multi-band pass filter of the image capture portion,
the multi-band pass filter dividing a visible spectrum into six contiguous and non-overlapping regions including right three pass bands being alternately contiguous with left three pass bands,
the right three pass bands being separated by right three stop bands that are identical to the left three pass bands, and the left three pass bands being separated by left three stop bands that are identical to the right three pass bands,
all edges of the right three stop bands coinciding with all edges of the left three pass bands, and all edges of the left three stop bands coinciding with all edges of the right three pass bands,
the right multi-band pass filter being joined with and contacts the left multi-band pass filter to fit over and entirely cover the single lens, and
the folded substrate consisting of the detector at an outer side of the first leg facing the single lens and the image processing portion at an outer side of the second leg opposite the first leg the processes the signals from the detector located at the outer side of the first leg.

11. The endoscope system of claim 10, further comprising an illumination source sequentially outputs the different color spectrum of light during each image illumination interval such that different color spectrums of light are output during any two successive image illumination intervals of the plurality of image illumination intervals.

12. A medical endoscope system that obtains three-dimensional images, the medical endoscope system comprising:
a stationary illumination multi-bandpass optical filter which sequentially passes a different color spectrum of light, of a plurality of color spectrums of light, during an image illumination interval;
an image capture portion which sequentially captures a plurality of images each corresponding with a different color spectrum of light which passes through the stationary illumination multi-bandpass optical filter;
an image processing portion which processes the sequentially captured plurality of images for each image illumination interval and forms corresponding 3D image information; and
a folded substrate folded into a U-shape having first and second legs,
the image capture portion including a right multi-band pass filter and a left multi-band pass filter, a detector and a single lens having a single continuous portion that entirely covers both the right multi-band pass filter and the left multi-band pass filter and directly receives the right image from the right multi-band pass filter and the left image from the left multi-band pass filter, the single lens directly providing the right image from the right multi-band pass filter and the left image from the left multi-band pass filter to the detector, the stationary illumination multi-band pass filter being identical to the right multi-band pass filter and the left multi-band pass filter of the image capture portion so that the stationary illumination multi-band pass filter has filter characteristics that are identical to filter characteristics of the right multi-band pass filter and the left multi-band pass filter of the image capture portion, the stationary illumination multi-band pass filter dividing a visible spectrum into six contiguous and non-overlapping regions including right three pass bands being alternately contiguous with left three pass bands, the right three pass bands being separated by right three stop bands that are identical to the left three pass bands, and the left three pass bands being separated by left three stop bands that are identical to the right three pass bands, all edges of the right three stop bands coinciding with all edges of the left three pass bands, and all edges of the left three stop bands coinciding with all edges of the right three pass bands, the right multi-band pass filter being joined with and contacts the left multi-band pass filter to fit over and entirely cover the single lens, and the folded substrate consisting of the detector at an outer side of the first leg facing the single lens and the image processing portion at an outer side of the second leg opposite the first leg that processes the signals from the detector located at the outer side of the first leg.

13. The medical endoscope system of claim 12, further comprising:
an illumination source sequentially outputs different color spectrums of light; and
a three dimensional display which renders the 3D image information.

14. The medical endoscope system of claim 12, wherein the stationary illumination multi-bandpass optical filter further comprises a disk having one or more openings forming pupils.

15. The medical endoscope system of claim 12, wherein the stationary illumination multi-bandpass filter is located at a distal end of the endoscope.

16. A method to obtain three dimensional images from an endoscope, the method comprising acts of:
sequentially passing a different color spectrum of light of a plurality of color spectrums of light through a stationary illumination multi-bandpass filter during an image illumination interval such that a different color of light is passed through the stationary illumination multi-bandpass filter during each image illumination interval of a plurality of image illumination intervals which form an image illumination period;
sequentially capturing by an image capture unit located on a folded substrate a plurality of images each corresponding with a different color spectrum of light which passes through the stationary illumination multi-bandpass filter during a corresponding image illumination interval of the plurality of image illumination intervals using an image capture portion; and
processing the sequentially captured plurality of images for each image illumination interval and forming corresponding 3D image information corresponding with the sequentially captured plurality of images using an image processing portion,
the image capture unit including a right multi-band pass filter and a left multi-band pass filter, a detector and a single lens having a single continuous portion that entirely covers both the right multi-band pass filter and the left multi-band pass filter and directly receives the right image from the right multi-band pass filter and the left image from the left multi-band pass filter, the single lens directly providing the right image from the right multi-band pass filter and the left image from the left multi-band pass filter to the detector, the stationary illumination multi-band pass filter being identical to the right multi-band pass filter and the left multi-band pass filter of the image capture unit so that the stationary illumination multi-band pass filter has filter characteristics that are identical filter characteristics of the right multi-band pass filter and the left multi-band pass filter of the image capture unit, the stationary illumination multi-band pass filter dividing a visible spectrum into six contiguous and non-overlapping regions including right three pass bands being alternately contiguous with left three pass bands, the right three pass bands being separated by right three stop bands that are identical to the left three pass bands, and the left three pass bands being separated by left three stop bands that are identical to the right three pass bands, all edges of the right three stop bands coinciding with all edges of the left three pass bands, and wherein all edges of the left three stop bands coinciding E with all edges of the right three pass bands, the right multi-band pass filter being joined with and contacts the left multi-band pass filter to fit over and entirely cover the single lens, and the folded substrate being folded into a U-shape having first and second legs and consisting of the detector at an outer side of the first leg facing the single lens and the image processing portion at an outer side of the second leg opposite the first leg that processes the signals from the detector located at the outer side of the first leg.

17. The method of claim 16, further comprising acts of:
sequentially outputting the different color spectrum of light during each image illumination interval such that different color spectrums of light are output during any two successive image illumination intervals of the plurality of image illumination intervals; and
rendering the 3D image information on a display of the system that displays three dimensional images.

18. The method of claim 16, further comprising an act of selectively controlling the stationary illumination multibandpass optical filter to pass only currently selected spectrum of light of the plurality of color spectrums of light each different from each other.

19. The method of claim 16, further comprising an act of synchronizing two or more of an illuminator, a multibandpass optical filter, and an image capture portion to operate synchronously with each other.

20. A method to obtain three dimensional images of an object from an endoscope, the method comprising acts of:
sequentially illuminating the object with a different color spectrum of light, of a plurality of color spectrums of light, during an image illumination interval using white light passing through a stationary illuminator multibandpass optical filter of an illuminator;
sequentially receiving reflected light from the object having the different color spectrum of light by a right pupil that receives a right image through a right multi-band pass filter having right three pass bands, and by a left pupil that receives a left image through a left multi-band pass filter having left three pass bands, the right multi-band pass filter having the right three pass bands being a complement of the left multi-band pass filter having left three pass bands, and the stationary illuminator multi-band pass optical filter of the illuminator being identical to the right multi-band pass filter of the right pupil and the left multi-band pass filter of the left pupil so that the stationary illuminator multi-band pass filter has filter characteristics that are identical to filter characteristics of the right multi-band pass filter of the right pupil and the left multi-band pass filter of the left pupil;

sequentially capturing a plurality of images corresponding with a different color spectrum of light which passes through the stationary illuminator multi-bandpass optical filter using an image capture portion located on a folded substrate and having a detector and a single lens having a single continuous portion that entirely covers both the right pupil and the left pupil and directly receives the right image from the right multi-band pass filter and the left image from the left multi-band pass filter;

processing the sequentially captured plurality of images for each image illumination interval and forming corresponding 3D image information using an image processing portion; and rendering the 3D image information on a display that displays three dimensional images, the stationary illuminator multi-band pass filter dividing a visible spectrum into six contiguous and non-overlapping regions including the right three pass bands being alternately contiguous with the left three pass bands, the right three pass bands being separated by right three stop bands that are identical to the left three pass bands, and the left three pass bands being separated by left three stop bands that are identical to the right three pass bands, all edges of the right three stop bands coinciding with all edges of the left three pass bands, and wherein all edges of the left three stop bands coinciding with all edges of the right three pass bands, the right multi-band pass filter being joined with and contacts the left multi-band pass filter to fit over and entirely cover the single lens, the single lens directly providing the right image and the left image to the detector, and the folded substrate being folded into a U-shape having first and second legs and consisting of the detector at an outer side of the first leg facing the single lens and the image processing portion at an outer side of the second leg opposite the first leg that processes the signals from the detector located at the outer side of the first leg.

21. The method of claim 20, further comprising situating the single lens at a distal end of the endoscope at an end of the endoscope and within a body barrel of the endoscope.

22. The method of claim 20, further comprising an act of forming the main body barrel of the endoscope to have proximal and distal ends and an outside diameter less than 6 mm at the distal end.

23. The method of claim 20, further comprising an act of situating the stationary illuminator multi-bandpass filter at a distal end of the endoscope.

24. The endoscope of claim 1, wherein the image capture device provides a front view when pointed in a front direction along a longitudinal axis of the housing and to rotate about an offset pivot axis to provide a rearward view which is opposite to the front view, wherein the offset pivot axis is offset with respect to the longitudinal axis.

25. The medical endoscope system of claim 12, wherein the image capture portion provides a front view when pointed in a front direction along a longitudinal axis of the image capture portion, and to rotate about an offset pivot axis to provide a rearward view which is opposite to the front view, wherein the offset pivot axis is offset with respect to the longitudinal axis.

26. The endoscope of claim 1, wherein the single lens that entirely covers both the right pupil and the left pupil is unpartitioned, and wherein the right multi-band pass filter and the left multi-band pass filter are integrated with the single lens.

27. The endoscope system of claim 10, wherein the single lens that entirely covers both the right pupil and the left pupil is unpartitioned, and wherein the right multi-band pass filter and the left multi-band pass filter are integrated with the single lens.

28. The medical endoscope system of claim 12, wherein the single lens that entirely covers both the right pupil and the left pupil is unpartitioned, and wherein the right multi-band pass filter and the left multi-band pass filter are integrated with the single lens.

29. The method of claim 16, wherein the single lens that entirely covers both the right pupil and the left pupil is unpartitioned, and wherein the right multi-band pass filter and the left multi-band pass filter are integrated with the single lens.

30. The method of claim 20, wherein the single lens that entirely covers both the right pupil and the left pupil is unpartitioned, and wherein the right multi-band pass filter and the left multi-band pass filter are integrated with the single lens.

31. The endoscope of claim 1, wherein the illuminator provides a first light through first illuminator right and left pass bands that are continuous, followed by a second light through second illuminator right and left pass bands that are continuous, followed by a third light through third illuminator right and left pass bands that are continuous.

32. An endoscope that provides a stereoscopic three dimensional image of a region of interest inside of a body, the endoscope comprising:

a housing having a distal end and a proximal end, the distal end being insertable into a cavity of the body;

an image capture device at the distal end that obtains optical images of the region of interest, and processing the optical images that forms video signals;

a folded substrate folded into a U-shape having first and second legs; and a connecting device between the image capture device and the proximal end that connects the image capture device to an illumination source and a display, the connecting device providing the video signals to the display that displays the optical images of the region of interest;

the image capture device comprising:
an illuminator that illuminates the region of interest with light,
a single lens that receives the light reflected from the region of interest,
a focal plane detector array that directly receives the light from the lens and obtaining the optical images from the single lens, and
processing circuits that processes signals from the focal plane detector array and forming the video signals,
the single lens being entirely covered with lens right and left conjugated multi-bandpass filters (CMBFs) that fit over the single lens,
the single lens directly receiving the light from the lens right and left CMBFs, and the illuminator providing the light through illuminator right and left CMBFs that are identical to the single lens right and left CMBFs, the folded substrate consisting of the focal plane detector array at an outer side of the first leg facing the single lens and the processing circuits at an outer side of the second leg facing the connecting device that processes the signals from the focal plane detector array located at the outer side of the first leg.

33. The endoscope of claim 32, wherein the lens right CMBF has right pass bands including a red-right pass band, a green-right pass band and a blue-right pass band, and the lens left CMBF has left pass bands including a red-left pass band, a green-left pass band and a blue-left pass band, the right pass bands being complements of the left pass bands, and wherein the illuminator provides a first light through first illuminator right and left CMBFs having the red-right pass band and the red-left pass band, followed by a second light through second illuminator right and left CMBFs having the green-right pass band and the green-left pass band, followed by a third light through third illuminator right and left CMBFs having the blue-right pass band and the blue-left pass band.

34. The endoscope of claim 1, wherein the right and left multi-band pass filters are removably placed on one of a front and a back surface of the single lens, for allowing removal of the CMBFs to perform monocular imaging.

35. The endoscope system of claim 10, wherein the right and left multi-band pass filters are removably placed on one of a front and a back surface of the single lens, for allowing removal of the CMBFs to perform monocular imaging.

36. The medical endoscope system of claim 12, wherein the right and left multi-band pass filters are removably placed on one of a front and a back surface of the single lens, for allowing removal of the CMBFs to perform monocular imaging.

37. The endoscope of claim 32, wherein the CMBFs are removably placed on one of a front and a back surface of the single lens, for allowing removal of the CMBFs to perform monocular imaging.

* * * * *